United States Patent [19]
Elder et al.

[11] Patent Number: 6,107,537
[45] Date of Patent: *Aug. 22, 2000

[54] DISPOSABLE ABSORBENT ARTICLES PROVIDING A SKIN CONDITION BENEFIT

[75] Inventors: Gretchen Louise Elder, Blue Ash; Donald Carroll Roe, West Chester, both of Ohio; Laura Graves Van Rijswijck, Burlington, Ky.; Mathias Kurt Herrlein, Frankfurt; Manfred Plischke, Steinbach/Ts., both of Germany; Julie Charlene Rule; George Christopher Dobrin, both of Cincinnati, Ohio; Edward John Milbrada, West Chester, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/926,566

[22] Filed: Sep. 10, 1997

[51] Int. Cl.$^7$ ..................................... A61F 13/15
[52] U.S. Cl. ................................ 604/364; 604/378
[58] Field of Search ................... 604/364, 358, 604/378

[56] References Cited

U.S. PATENT DOCUMENTS

| | | | |
|---|---|---|---|
| 3,464,413 | 9/1969 | Goldfarb et al. | 128/268 |
| 3,489,148 | 1/1970 | Duncan et al. | 128/284 |
| 3,585,998 | 6/1971 | Hayford et al. | 128/284 |
| 3,896,807 | 7/1975 | Buchalter | 128/261 |
| 3,989,867 | 11/1976 | Sisson | 428/132 |
| 4,578,069 | 3/1986 | Whitehead et al. | 604/370 |
| 4,627,847 | 12/1986 | Puletti et al. | 604/366 |
| 4,648,876 | 3/1987 | Becker et al. | 604/370 |
| 4,713,068 | 12/1987 | Wang et al. | 604/366 |
| 4,713,069 | 12/1987 | Wang et al. | 604/378 |
| 4,758,339 | 7/1988 | Vellinga | 210/188 |
| 4,798,603 | 1/1989 | Meyer et al. | 604/378 |
| 4,833,172 | 5/1989 | Schwarz et al. | 521/62 |
| 4,898,642 | 2/1990 | Moore et al. | 162/157.6 |
| 4,902,553 | 2/1990 | Hwang et al. | 428/156 |
| 4,923,650 | 5/1990 | Antoon, Jr. et al. | 264/41 |
| 5,254,111 | 10/1993 | Cancio et al. | 604/385.1 |
| 5,492,751 | 2/1996 | Butt, Sr. et al. | 428/198 |
| 5,525,346 | 6/1996 | Hartung et al. | 424/402 |
| 5,599,420 | 2/1997 | Yeo et al. | 156/290 |
| 5,607,760 | 3/1997 | Roe | 442/375 |
| 5,628,737 | 5/1997 | Dobrin et al. | 604/383 |
| 5,643,588 | 7/1997 | Roe et al. | 424/402 |
| 5,855,999 | 1/1999 | McCormack . | |

FOREIGN PATENT DOCUMENTS

| | | | |
|---|---|---|---|
| 0 315 013 | 5/1989 | European Pat. Off. . | |
| 0 422 504 A2 | 4/1991 | European Pat. Off. | A61F 13/15 |
| 0 640 330 A1 | 3/1995 | European Pat. Off. | A61F 13/46 |
| 0 710 471 A1 | 5/1996 | European Pat. Off. | A61F 13/15 |
| 0 397 110 B1 | 7/1996 | European Pat. Off. | A61F 13/46 |
| WO 90/10424 | 9/1990 | WIPO | A61F 13/00 |
| WO 95/16562 | 6/1995 | WIPO | B32B 5/24 |
| WO 95/16746 | 6/1995 | WIPO | C08L 67/02 |
| WO 98/58607 | 12/1998 | WIPO . | |

*Primary Examiner*—John G. Weiss
*Assistant Examiner*—Catherine Cogut
*Attorney, Agent, or Firm*—Edward J. Milbrada; Caroline Wei-Berk; Steven W. Miller

[57] ABSTRACT

The present invention relates to absorbent articles which provide improved protection against skin overhydration. A particularly preferred embodiment of an absorbent article of the present invention comprises a body contacting surface having a skin care composition thereon that, when at least a portion of the composition is transferred to a wearer's skin by normal body motion or body heat, the material is effective in providing a skin condition benefit and a liquid impermeable, breathable backsheet having a mass vapor transmission rate value (MVTR) of at least about 1300 $g/m^2/24$ hr and an absorbent core having a post acquisition collagen rewet method value (PACORM) with a PACORM: MVTR ratio is less than 0.05 $mg/(g/m^2/24\ hr)$.

19 Claims, 5 Drawing Sheets ness articles, catamenial devices, training pants, and the like. In particular, the present invention relates to disposable absorbent articles which provide improved protection against skin overhydration because of a skin care composition disposed on the topsheet thereof at least a portion of which composition transfers to a wearer's skin to provide a barrier against excess environmental moisture; improved skin aeration, such as is provided by improved backsheet breathability; and superior liquid handling performance.

DISPOSABLE ABSORBENT ARTICLES PROVIDING A SKIN CONDITION BENEFIT

FIELD OF THE INVENTION

The present invention relates to disposable absorbent articles such as diapers, incontinence articles, catamenial devices, training pants, and the like. In particular, the present invention relates to disposable absorbent articles which provide improved protection against skin overhydration because of a skin care composition disposed on the topsheet thereof at least a portion of which composition transfers to a wearer's skin to provide a barrier against excess environmental moisture; improved skin aeration, such as is provided by improved backsheet breathability; and superior liquid handling performance.

BACKGROUND OF THE INVENTION

Disposable absorbent articles such as diapers, incontinence articles, catamenial devices, training pants and the like are well known in the art. Typically, disposable absorbent articles comprise a liquid pervious topsheet that faces the wearer's body, a liquid impervious backsheet that faces the wearers clothing, an absorbent core disposed between the liquid previous topsheet and the backsheet, and means to keep the core in fixed relation to the wearer's body.

In order to absorb and contain bodily exudates such as urine, feces or menstrual fluids, an absorbent article must cover (i.e. occlude) certain parts of a wearer's body. Generally, current absorbent articles cover even larger parts of the wearer's body than may be necessary for absorption alone to allow for adequate storage of the exudates and to maintain the absorbent article in a proper position relative to the wearers body for such absorption.

While this coverage is an essential element of the functionality of the article, skin occlusion due to wearing the article also can, in addition to negatively impacting wearer comfort, cause negative changes to wearer skin structure. For example the pressure exerted by elastic elements in absorbent articles of the current art can cause red marking. Also, occlusion of the skin by the absorbent article can, potentially, lead to skin overhydration with resulting increased risk of skin irritation. Further, as skin becomes overhydrated, it becomes macerated. As a result, overhydrated skin is more susceptible to damage from abrasion due to rubbing caused by normal wearer movements (i.e. chafing). Such susceptibility to skin disorders, including diaper rash, erythema (i.e. redness), heat rash, abrasion, pressure marks and skin barrier loss is well known. For example, 21 C.F.R. 333.503 defines diaper rash "[a]n inflammatory skin condition in the diaper area (perineum buttocks, lower abdomen, and inner thighs) caused by one or more of the following factors: moisture, occlusion, chafing, continued contact with urine or feces or both, or mechanical or chemical irritation."

Said another way, the stratum corneum is the skin layer that, almost exclusively, provides the water barrier properties to the skin. Thus, any environmental condition that can increase the hydration state of the stratum corneum will, in all likelihood, lead to overhydration. As noted above, occlusion by an absorbent article is a prime example of an environmental condition that can lead to overhydration. In particular, skin occluded by an absorbent article sees at least the following differences in its environment when compared to unoccluded skin:

Available water from bodily fluids, such as urine, increases the driving force across the extra cellular lipid component of the stratum corneum (the hydrophobic component which provides the main water barrier properties to the stratum corneum) allowing the keratin enriched corneocyte component of the stratum corneum (the hydrophilic component which provides mechanical strength to the stratum corneum) to become overhydrated. Such available water can come from inadequate acquisition by the absorbent article, from rewet because the absorbent article falls to have adequate liquid retention capability or from sweat due to the occlusive nature of the absorbent article.

Increased relative humidity in the void volume between the absorbent article and the skin can interfere with the natural transport of water vapor into and out of the skin. As is well known, mass transport depends on a concentration differential across a barrier. If the relative humidity on the outside of the stratum corneum becomes too high and additional water is delivered to the body side of the stratum corneum (e.g. due to an increase in ambient temperature) the water will remain in/on the skin a longer period of time.

Once the skin begins to become overhydrated, the barrier properties of the extra cellular lipid component of the stratum corneum begin to degenerate.

Such degeneration results in increased overhydration, leading to compromised skin and, even, diaper rash (diaper dermatitis).

While the art has approached this problem in various ways (see below), it has failed to recognize that improving protection against skin overhydration due to wearing an absorbent article (i.e. maintaining the skin occluded by an absorbent article in a state more like the state of unoccluded skin) is multifunctional in nature. As is discussed in the various objects for the present invention, skin can best be protected against overhydration by addressing all (or as many as possible) of the sources of overhydration at one time.

Numerous attempts have been disclosed that are directed to improving wearer skin condition by reducing the risk of creating overhydrated skin or by allowing already overhydrated skin to dehydrate to a level closer to unoccluded skin. For example:

More or less breathable devices or materials are described in U.S. Pat. Nos. 4,627,847, 4,648,876, 4,578,069, 4,713,068, 4,758,339, 4,833,172, 4,923,650, 5,254,111, 5,492,751, 5,599,420 and 5,628,737, in published European Patent applications EP 315,013 and EP 710,471, and in published PCT applications WO 95/16,562 and WO 95/16,746. Generally, all such devices or materials balance gas permeability and liquid impermeability. This becomes particularly apparent when considering materials having apertures or pores, whereby an increase in pore size will allow easier gas permeation, but also easier liquid permeation. The latter may be undesirable, in particular, when such materials are used as backsheet materials to cover liquid retaining regions of an absorbent article, such as the core region thereof In particular, for articles designed to absorb larger quantities of liquids, such as baby or adult incontinence devices, approaches aimed at keeping only part of the article breathable, such as by covering the liquid absorbing parts (often referred to as absorbent core) by a non-breathable material, but having other parts of the article made of breathable materials have been used.

The art has also used "lotions" in combination with absorbent articles. Examples include: U.S. Pat. No. 3,585,998 to Hayford et al.; U.S. Pat. No. 3,464,413 to Goldfarb et al.; U.S. Pat. No. 3,896,807 to Buchalter; U.S. Pat. No. 3,489,148 to Duncan et al.; and U.S. Pat. No. 5,643,588 to Roe et al. While such attempts may provide a "lotion", devices of the current art have either failed to transfer an amount of lotion that is effective against overhydration or to even recognize that lotion applied to an absorbent article may be effective against overhydration.

The art has also focused on providing absorbent cores that are effective in acquiring, distributing, and storing discharges of bodily fluids. Such devices are described in, for example: U.S. Pat. Nos. 4,898,642 and 4,798,603; Published European Patent applications EP 640,330 and EP 397,110; and in many other patents and published applications. In previous attempts aimed at improving the interaction between absorbent articles and the skin of the wearer, the art has not sufficiently recognized that there can be cooperation between good rewet performance of the absorbent article and material transport through backsheet materials which can result in improved skin condition.

While, as is clear from the above, the art has continually attempted to improve various individual aspects of absorbent articles, as such aspects may relate to maintaining a wearer's skin in a condition more like that of unoccluded skin, the art has failed to recognize that such aspects may cooperate to provide even further improvement in wearer skin condition.

Thus, it is an object of the present invention to provide disposable absorbent articles that provide a skin condition benefit to a wearer's skin. In particular, it is an object of the present invention to provide absorbent articles that help maintain a wearer's skin at a hydration level that is more like the hydration level of unoccluded skin than absorbent articles of the current art. It is a further object of the present invention to provide such hydration level maintenance by providing absorbent articles having cores with particularly good fluid handling performance (in particular the rewet characteristics of such cores). It is still a further object of the present invention to provide such absorbent articles with vapor permeable backsheet materials so as to reduce the relative humidity in the void volume between the absorbent article and a wearer's skin. It is yet a further object of the present invention to provide such absorbent articles with a body contacting surface (e.g. a topsheet, a cuff, or the like) comprising a skin care composition at least a portion of which can transfer from the body contacting surface to a wearer's body to provide a skin condition benefit (e.g., providing a barrier to any residual moisture remaining on the wearer's skin so such residual moisture is less deleterious to the wearer's skin condition). It is still a further object of the present invention to provide a single absorbent article comprising such improved absorbent cores, such permeable backsheets, and such topsheets. These and other objects may be obtained by using the present invention as will be taught in the following disclosure.

SUMMARY OF THE INVENTION

The present invention relates to absorbent articles which provide improved protection against skin overhydration. That is, such articles help maintain the skin of an individual wearing the absorbent article of the present invention in a condition more like unoccluded skin. A particularly preferred embodiment of an absorbent article of the present invention comprises a body contacting surface having a skin care composition thereon that, when at least a portion of the composition is transferred to a wearer's skin by contact, normal body motion, body heat, or combinations thereof, the material is effective in providing a skin condition benefit and a backsheet having a MVTR of at least about 500 $g/m^2/24$ hr. An alternative preferred embodiment of the absorbent article further comprises a liquid impermeable, breathable backsheet having a mass vapor transmission rate value (MVTR) of at least about 1300 $gm^2/24$ hr and an absorbent core having a post acquisition collagen rewet method value (PACORM) wherein the PACORM:MVTR ratio is less than 0.050 $mg/(glm^2/24$ hr).

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

Absorbent Articles: General Discussion

As used herein, the term "absorbent article" refers to devices which absorb and contain body exudates, and, more specifically, refers to devices which are placed against or in proximity to the body of the wearer to absorb and contain the various exudates discharged from the body.

The term "disposable" is used herein to describe absorbent articles which are not intended to be laundered or otherwise restored or reused as an absorbent article (i.e., they are intended to be discarded after use and, preferably, to be recycled, composed or otherwise disposed of in an environmentally compatible manner).

As used herein, the term "skin care composition" refers to any composition which comprises one or more agents which, when transferred from an absorbent article to a wearer's skin, provide a therapeutic or protective skin benefit. Representative materials are discussed in detail below.

As used herein, the term "treated article" means an absorbent article having a skin care composition on or migratable to at least one body contacting surface of that article.

As used herein, the term "body contacting surface" of an absorbent article is one or more surfaces of any article components that contact the wearer at some time during the wear period. Body contacting surfaces include, but are not limited to, portions of the topsheet, leg cuffs, waist region, side panels, fastening tabs, etc., which contact a wearer during use.

Other terms are defined in the specification where initially discussed.

All percentages, ratios and proportions used herein are by weight unless otherwise specified.

Figure 1:
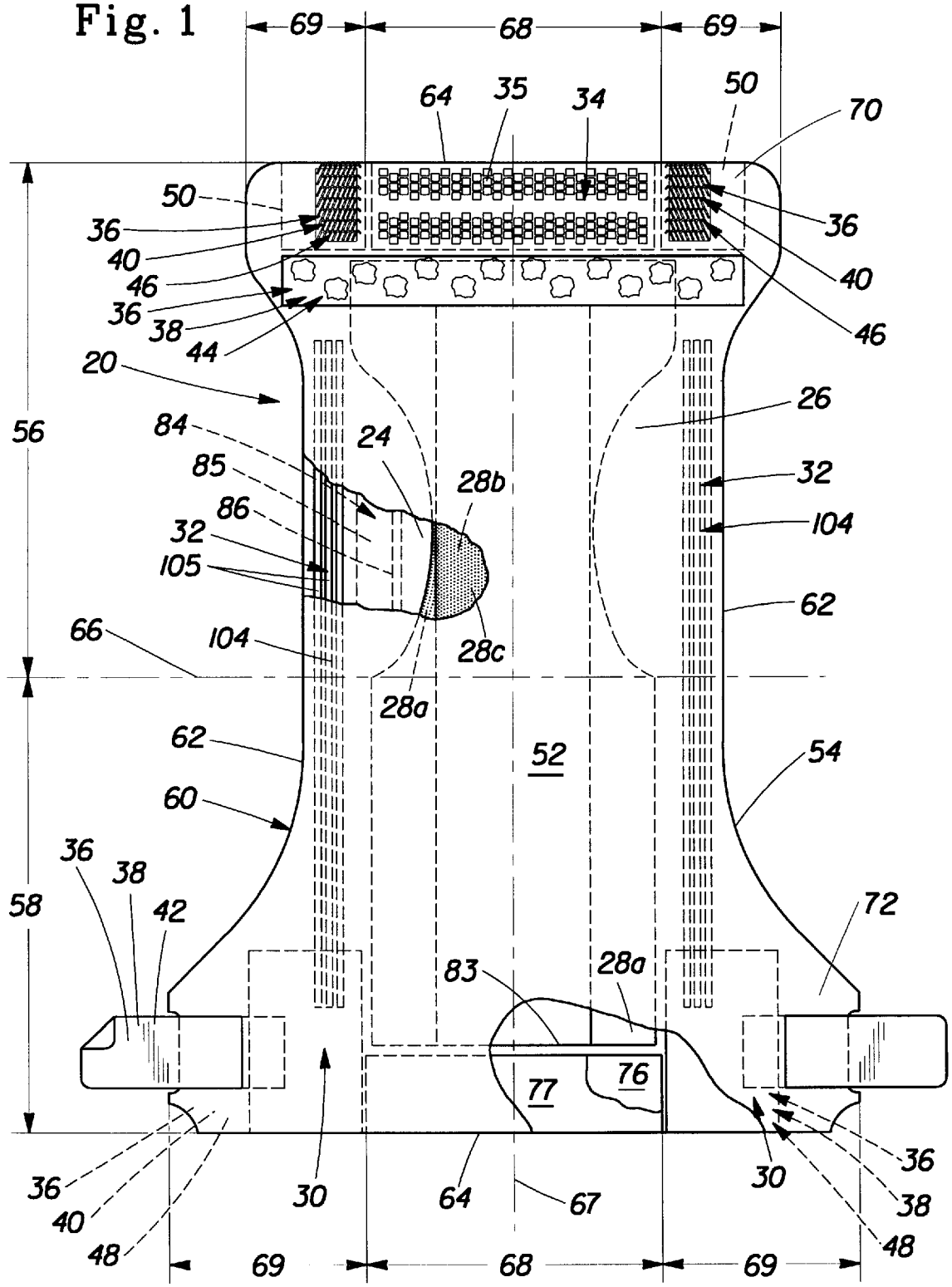
FIG. 1 is a plan view of an absorbent article of the present invention in the form of a diaper.
Figure 2:
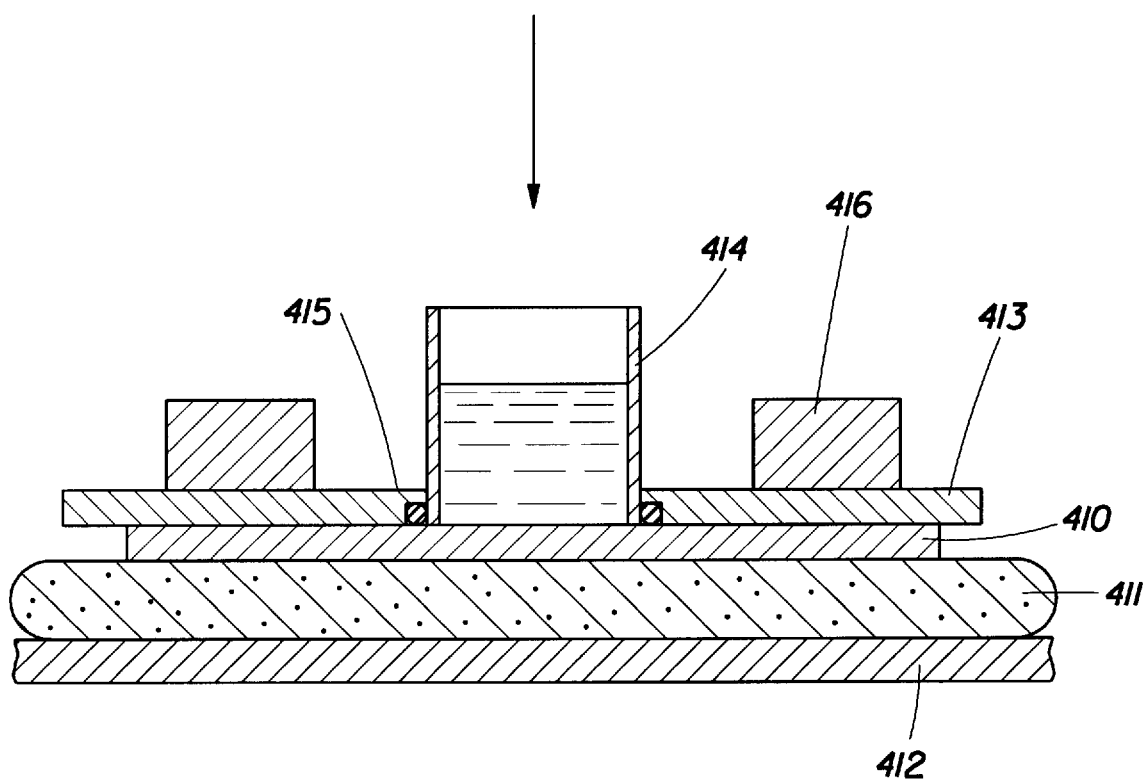
FIG. 2 is a schematic drawing showing the test set up for the acquisition Test described in the TEST METHODS section.

Within the context of the present invention and with reference to FIG. 1, a preferred absorbent article 20 comprises:

a) a central region 68 (which may consist of substructures and/or wrapping materials), including on the side oriented towards the wearer a topsheet 24, which forms the inner or body surface and which, at least in certain regions thereof allows bodily exudates to penetrate therethrough, and includes on the opposite side a backsheet 26 which forms the outer or garment surface of the article and which separates the absorbent core from the surrounding environment, such as the clothing of the wearer.

b) a chassis region 69 comprising features such as closure elements and elastically extensible elements to maintain the article on the wearer. The chassis region 69 also comprises a topsheet 24 which forms the inner or body-contacting surface thereof and a backsheet 26.

The backsheet and the topsheet materials of the central region 68 can be unitary with respective materials in the chassis region 69, i.e. the backsheet 26 can cover the absorbent core 28 and the same material or sheet may extend into the chassis region 69 or the topsheet 24 and the backsheet 26 can comprise different materials in each of the central region 68 and the chassis region 69.

FIG. 1 is a plan view of a diaper embodiment of an absorbent article of the present invention. The diaper 20 is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a liquid pervious, topsheet 24, a liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer or garment surface 52 (facing the viewer in FIG. 1), an inner or body contacting surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central or central region 68 and chassis region 69. The chassis region 69 comprises a pair of laterally extending side panels 70, 72 which typically comprise the outer lateral portions of the waist regions 56, 58. The side panels positioned in the first waist region 56 are designated 70 while the side panels positioned in the second waist region 58 are designated 72. While it is not necessary that the laterally opposed pairs of side panels 70, 72 be identical, they are preferably mirror images one of the other. The side panels 72 positioned in the second waist region 58 can be elastically extensible in the lateral direction (thus forming elasticized side panels 30).

The lateral direction (x direction or width) is defined as the direction parallel to the lateral centerline 66 of the diaper 20. The longitudinal direction (y direction or length) is defined as the direction parallel to the longitudinal centerline 67. The axial direction (z direction or thickness) being defined as the direction perpendicular to the outer surface 52 and extending through the thickness of the diaper 20.

FIG. 1 shows a specific execution of the diaper 20 in which the topsheet 24 and the backsheet 26 are unitary across the core and the chassis region and have length and width dimensions generally larger than those of the absorbent core 28. The topsheet 24 and the backsheet 26 extend beyond the edges of the absorbent core 28 and thereby form the periphery 60 of the diaper 20. The periphery 60 defines the outer perimeter or, in other words, the edges of the diaper 20. The periphery 60 comprises the longitudinal edges 62 and the end edges 64.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in U.S. Pat. No. 4,909,803, which issued to Aziz, et al. on Feb. 24, 1989. In a preferred embodiment, the elasticized leg cuff 32 additionally comprises an elastic gasketing cuff 104 with one or more elastic strands 105, positioned outboard of the barrier cuff 84 such as described in U.S. Pat. No. 4,695,278, which issued to Lawson on Sep. 22, 1987.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region.

The elasticized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76. Such mechanically stretched waist features are described in U.S. Pat. No.

5,151,092, issued to Buell, et al. on Sep. 29, 1992, the disclosure of which is incorporated herein by reference.

This as well as other components of the diaper are given in more detail in U.S. Pat. No. 5,234,423, issued to Buell, et al. on Aug. 10, 1993, the disclosure of which is incorporated herein by reference.

Absorbent Core: Core Structure

The absorbent core 28 should be generally compressible, conformable, non-irritating to the wearer's skin, and capable of absorbing and retaining liquids such as urine and other certain body exudates. The absorbent core 28 may comprise a wide variety of liquid absorbent or liquid handling materials commonly used in disposable diapers and other absorbent articles such as, but not limited to, comminuted wood pulp which is generally referred to as airfelt; meltblown polymers including coform; chemically stiffened, modified or crosslinked cellulosic fibers; tissue including tissue wraps and tissue laminates. Alternatively the absorbent core 28 may comprise other porous materials, such as foams, either alone or in combination with such fibrous webs as may be suitable as a core material.

Examples for absorbent structures are described in U.S. Pat. No. 4,610,678, issued to Weisman et al. on Sep. 9, 1986; U.S. Pat. No. 4,673,402, issued to Weisman et al. on Jun. 16, 1987; U.S. Pat. No. 4,888,231, issued to Angstadt on Dec. 19, 1989; U.S. Pat. No. 5,180,622, (Berg et al.); U.S. Pat. No. 5,102,597 (Roe et al.); U.S. Pat. No. 5,387,207 (LaVon) and in EP Patent Application 640,330, published in the name of Plischke, et al. on Mar. 1, 1995. Such structures can be adapted to be compatible with the requirements outlined below to be suitable for use as an absorbent core 28 of the present invention.

The absorbent core can be a unitary core structure, or it can be a combination of several absorbent structures, which in turn can consist of one or more sub-structures. Each of the structures or sub-structures can have an essentially two-dimensional extension (i.e. be a layer) or a three-dimensional shape.

The diaper 20 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Absorbent Core Materials-Fibrous Materials

The absorbent core 28 of the present invention may comprise fibrous materials which form a fibrous web or a fibrous matrix. Fibers useful in the present invention include naturally occurring fibers, such as wood or cotton fibers. Such natural fibers may be modified or unmodified. Also suitable are synthetic fibers, such as polyethylene and polypropylene fibers. For many absorbent cores or core structures according to the present invention, hydrophilic fibers are preferred. This preferred hydrophilicity can be obtained by using hydrophilic starting materials or by hydrophilicing naturally hydrophobic fibers. Naturally hydrophobic fibers such as thermoplastic fibers derived from polyolefins can be rendered hydrophilic by an appropriate treatment as is known to the art (i.e. such fibers may be surfactant-treated or silica-treated).

Suitable naturally occurring fibers are wood pulp fibers which can be obtained from well-known chemical processes such as the Kraft and sulfite processes. Also chemically stiffened cellulosic fibers are suitable. For example, crosslinking agents can be applied to the fibers so that, subsequent to application, intrafiber chemical crosslinks which can increase the stiffness of the fibers are formed. While the use of such intrafiber crosslink bonds to chemically stiffen the fiber is preferred, it is not meant to exclude other types of reactions which may stiffen such fibers. Fibers stiffened by crosslink bonds in individualized form (i.e., the individualized stiffened fibers, as well as process useful for their preparation) are disclosed, for example, in U.S. Pat. No. 3,224,926; U.S. Pat. No. 3,440,135; U.S. Pat. No. 3,932,209; and U.S. Pat. No. 4,035,147; U.S. Pat. No. 4,898,642; and U.S. Pat. No. 5,137,537.

Thermoplastic fibers may also be used in certain embodiments of the absorbent structures of the present invention. Such fibers can be made from any thermoplastic polymer that can be melted at temperatures that will not extensively damage the fibers or, alternatively, spun from a suitable solvent. The preferred thermoplastic fibers can be made from a variety of thermoplastic polymers, such as polyolefins (e.g. polyethylene or polypropylene). As discussed above, the surface of a hydrophobic thermoplastic fiber can be rendered hydrophilic by treatment with a surfactant. Suitable surfactants include non-ionic or anionic surfactants. Suitable non-ionic surfactants include surfactants such as Brij® 76 manufactured by ICI Americas, Inc. of Wilmington, Del., and various surfactants sold under Pegosperse® trademark by Glyco Chemical, Inc. of Greenwich, Conn. As noted above, anionic surfactants can also be used.

Such surfactants may be applied to the hydrophobic polymeric fibers using means known to the art (e.g., by spraying the fiber with a surfactant, by dipping the fiber into a surfactant or by including the surfactant as part of the polymer melt in producing the thermoplastic fiber). These surfactants can be applied to the thermoplastic fibers at levels of, for example, from about 0.2 to about 1 gram per square centimeter of thermoplastic fiber.

Suitable thermoplastic fibers can be made from a single polymer (mono-component fibers), or can be made from more than one polymer (e.g., bi-component fibers). For example, "bi-component fibers" can refer to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bi-component fibers provide thermal bonding due to melting, of the sheath polymer, while retaining the desirable strength characteristics of the core polymer. Suitable bicomponent fibers can also comprise two different polymeric materials having other spatial relationships than the core and sheath relationship discussed above. For example, the polymeric materials could be disposed in a side by side relationship.

In the case of thermoplastic fibers, their length can vary depending upon the particular melt point and other properties desired for these fibers. Typically, these thermoplastic fibers have a length between about 0.3 and about 7.5 cm, preferably between about 0.4 and about 3.0 cm. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters or dtex). Depending on the specific arrangement within the structure, suitable thermoplastic fibers can have a decitex in the range from about 0.4 dtex to about 20 dtex.

Such fibrous materials may be used in an individualized form when the absorbent article is being produced wherein an airlaid fibrous structure is formed on the absorbent article production line. Such fibers may also be used in the form of a preformed fibrous web or tissue. These preformed structures are then delivered to an absorbent article production line essentially in an effectively endless or very long form (e.g. on a roll or spool) and are cut to the appropriate size during production of the absorbent article. When multiple materials are used to form an absorbent structure such delivery and cutting can be done on each of such materials individually before these are combined with other materials to form the absorbent core 28. Alternatively, such materials may be delivered and combined before an individual core 28 is cut. Combination methods may also be used. There is a wide variety of methods for making such webs or tissues, and such processes are very well known in the art.

Absorbent Core Materials-Superabsorbent Polymers or Hydrogels

Optionally, and often preferably, the absorbent structures according to the present invention can comprise superabsorbent polymers, or hydrogels. The hydrogel-forming absorbent polymers useful in the present invention include a variety of substantially water-insoluble, but water-swellable polymers capable of absorbing large quantities of liquids. Such polymer materials are also commonly referred to as "hydrocoloids", or "superabsorbent" materials. These hydrogel-forming absorbent polymers preferably have a multiplicity of anionic, functional groups, such as sulfonic acid, and more typically carboxy groups. Examples of polymers suitable for use herein include those which are prepared from polymerizable, unsaturated, acid-containing monomers.

Hydrogel-forming absorbent polymers suitable for the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Particularly preferred polymeric materials for use in making hydrogel-forming particles are slightly network crosslinked polymers of partially neutralized polyacrylic acid and starch derivatives thereof Most preferably, the hydrogel-forming particles comprise from about 50 to about 95%, preferably about 75%, neutralized, slightly network crosslinked, polyacrylic acid (i.e. poly sodium acrylate/ acrylic acid).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures. Processes for network crosslinking the polymers and typical network crosslinking agents are described in greater detail in the herein before-referenced U.S. Pat. No. 4,076,663, and in U.S. Pat. No. 5,409,771, issued to Dahmen, et al. on Jun. 9, 1995.

The superabsorbent materials can be used in particulate form or in fibrous form and may also be combined with other elements to form preformed structures.

While the individual elements have been disclosed separately, an absorbent structure or substructure can be made by combining one or more of these elements.

Design Capacity and Ultimate Storage Capacity

In order to be able to compare absorbent articles for varying end use conditions, or differently sized articles, the "design capacity" of the article has been found to be a suitable measure. For example, babies are a typical user group, but even within this group the amount of urine loading, frequency of loading, composition of the urine will vary not only by age, i.e. from smaller babies (new-born babies) to toddlers on one side, but also among various individuals. Another user group may be larger children, still suffering from urinary incontinence. Also, incontinent adults can use such articles. Again, as with infants, there is a wide range of loading conditions, generally referred to as light incontinence ranging up to and including severe incontinence.

While one skilled in the absorbent products art will readily be able to transfer the teaching to other sizes, the following discussion will focus on toddler sized babies (i.e. babies weighing more than about 20 pounds (9 kg) and less than about 40 pounds (18 kg)). For such users, urine loadings of up to about 75 ml per voiding, with an average of four voids per wearing period are typical. Such a voiding pattern results in a total loading of up to about 300 ml. Voiding rates of 15 ml/sec have also been found to be representative of such wearers. As a result, absorbent articles, in order to be able to cope with such requirements should have the capability of acquiring and storing such amounts of urine, which as used herein with respect to the present invention will be referred to as the "design capacity" of the absorbent article. For purposes of applying the present invention to absorbent articles designed for different wearers which may have differing absorbency requirements, one skilled in the art will be able to readily adopt the appropriate design capacities for such user groups.

Such amounts of bodily fluids have to be acquired and absorbed by materials which can ultimately store the bodily fluids, or at least the aqueous components thereof, such that, little, if any, fluid remains on the surface of the article adjacent a wearers skin. The term "ultimate" refers, in one aspect, to the situation seen in an absorbent article after long wearing times, and, in another aspect, to absorbent materials in such absorbent articles which reach their "ultimate" capacity (i.e. are in equilibrium with their environment). As many of the processes under consideration have asymptotic kinetic behavior, one skilled in the art will readily recognize that "ultimate" capacities are reached when the actual capacity has reached a value sufficiently close to an asymptotic endpoint (e.g. change in capacity with time is of the same order as equipment measurement accuracy).

An absorbent article can comprise materials which are primarily designed to ultimately store bodily fluids. Such articles can also comprise other materials which are primarily designed for other functions, such as acquisition and/or distribution of bodily fluids, such other materials may still also have a certain ultimate storage capability. Suitable core materials according to the present invention are described without attempting to artificially separate such functions. Nonetheless, the ultimate storage capacity can be determined for the total absorbent core 28, for regions thereof, for absorbent structures, sub-structures, and even materials as may be a component of an absorbent core or structure.

In order to determine or evaluate the ultimate storage capacity of an absorbent article, a number of methods have been proposed. In the context of the present invention, it is assumed, that the ultimate storage capacity of an absorbent article is the sum of the ultimate capacities of the individual elements or material which the article comprises. For these individual components, various well established techniques can be applied, as long as they are applied consistently. For example, the Tea Bag Centrifuge Capacity (see TEST METHODS section), which has been developed and is well established for superabsorbent polymers, can be used for such materials. Once the capacities for the individual materials are known, the total article ultimate storage capacity can be calculated by multiplying these values (in ml/g) with the weight of the material used in the article. For materials having a dedicated functionality other than ultimate storage of fluids, such as acquisition layers and the like, the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

Given the discussion above, panty liners exhibit very low ultimate storage capacities (typically a few milliliters or less); catamenial pads have an ultimate storage capacity of up to about 20 ml; light urinary incontinence articles have an ultimate storage capacity of between about 75 ml and about 90 ml; medium urinary incontinence articles, and smaller size baby diapers can have an ultimate storage capacity of about 165 ml; toddler size baby diapers have ultimate storage capacities reaching 300 ml or more; and severe adult incontinence article have a 600 ml or more of ultimate storage capacity.

Absorbent cores 28 of the present invention have the additional benefit of very low rewet. Such cores 28 preferably comprise an acquisition layer 28a, an acquisition/distribution layer 28b, an a storage core 28c. The preferred cores 28 of the present invention are shown in FIG. 1 as having a structure wherein the acquisition/distribution layer 28b overlies the storage core 28c and the acquisition layer 28a is disposed between the acquisition/distribution layer 28b and the topsheet 24. The Post Acquisition Collagen Rewet Method (PACORM) has been found to describe this low rewet performance well (see TEST METHODS section below). In this test, current art cores have PACORM values of 150 mg and more; medium rewet performance cores have PACORM values between about 110 mg and about, 150 mg; cores with good rewet performance have PACORM values between about 110 mg and about 80 mg and cores with very good rewet performance have PACORM values of less than 80 mg. Cores 28 having even lower PACORM rewet values (e.g. less than 72 mg) are even more preferable.

Breathable Backsheet Materials

An essential element of the present invention is the use of materials which are sufficiently permeable to gases, such as air, water vapor, or other volatile materials. Apart from diffusion, gases or vapor can pass through a solid material by small capillary transport (slow), or convective transport (fast). Permeability can be assessed by the well known Mass Vapor Transmission Rate (MVTR), expressed in units of g 24 h/m² under various driving forces. For purposes of the present invention, the method, as is described in the TEST METHODS section below, involves calcium chloride which adsorbs moisture passing through the test specimen that is exposed to an environmental relative humidity of 75% at 40° C. An alternative method of assessing gas permeability uses an air permeability test (also described in the TEST METHODS section below), whereby air is sucked through a test specimen under defined conditions such as a specific pressure drop across the sample. As the air permeability test relates to high penetration rates, it is more applicable to materials allowing convective flow (fast) rather than the diffusional or capillary transport dominated (slow) materials.

A suitable material for use as a breathable backsheet for purposes of there present invention has a MVTR value of at least about 500 g/24 h/m². Preferably, the MVTR of breathable backsheet materials of the present invention is at least about 900 g/24 h/m². More preferably, the MVTR of the breathable backsheet material is also least 1300 g/24 h/m². Examples of such materials suitable for use in the present invention include:

Microporous films, for example as can be provided by Mitsui Toatsu Co., Japan under the designation ESPOIR NO or by EXXON Chemical Co., Bay City, Tex., under the designation EXXARE. Such films can be made by producing a polymer film (e.g. a polyethylene film which further comprises filler particles (e.g. calcium carbonate). After having formed a film wherein the filler particles are embedded into a polymer matrix, the film can be mechanically treated so as to permanently strain and stretch the polymerize. materials, thereby creating small cracks around the non-deforming filler particles. This deformation can be achieved by a number of different ways, in machine direction of the material such as by conventional stretching between two nip roll arrangements running at a differential speed, or in directions such as tentering fixing the edges of the material in diverging frames, or by running it through narrowly intermeshing rolls, or by any combination thereof. Each off these steps can be executed while the material is heated (i.e. at a temperature exceeding the ambient temperature, i.e. most often at temperature of more than about 40° C.), or "cold", i.e. below said temperature. The microporosity of such materials can be imparted as an integral process step of the film making process, as a separate process step, or as a process step which is integrated into further conversion of such materials, such as when using such films to produce absorbent articles. The cracks are sufficiently large to allow gas molecules or the gas phase of a liquid to pass through, but small enough to prevent liquids from penetrating. Thus the transport mechanisms is slow flow in capillaries.

Films or composites which comprise a mixture of (a) a block copolyether ester, a block copolyether amide and/or a polyurethane, (b) a thermoplastic homo, co or terpolymer that is incompatible with (a), and (c) a compatibilizer. Such materials are described in PCT application WO 95/16746, published on Jun. 22, 1995 in the name of E. I. DuPont. Composite materials comprising such polymer blends are available from Clopay Corporation, Cincinnati, Ohio under the name HYTREL blend P18-3097. Suitable materials of this type are also described in greater detail in copending U.S. patent application Ser. No. 08/744,487, filed on Nov. 6, 1996 in the name of Curro, the disclosure of which is incorporated herein by reference.

and

Apertured films as are discussed in U.S. Pat. No. 3,989,86 issued to Sisson on Nov. 2, 1976 which teaches a breathable backsheet provided with tapered hollow bosses which prevent the passage of liquids while allowing vapors to readily pass.

In order to be suitable as a backsheet 26 for the present invention, any of these materials must be both sufficiently permeable to gasses or vapors, as measured by MVTR and sufficiently impermeable to liquids such as water as measured by hydrostatic head (see TEST METHODS section).

Further, when using plastic film materials, it has often been found, that the plastic feel thereof is not preferred by consumers. As a result, it is often desirable to provide an improved hand to such materials. For example, hand can be improved by, among other ways, combining a layer of a suitable fibrous material, such as a low basis weight nonwoven, with the film to form a laminated structure. Such layers can be attached to the film by various methods as may be known to the art, such as using adhesives or by thermally joining the film and nonwoven material.

With respect to the present invention, films manufactured or treated to be permeable can be classified as follows:

TABLE 1

| Permeability Range | MVTR (g/m$^2$/24 h) |
| --- | --- |
| non-permeable | up to about 200 |
| low permeability | about 200–500 |
| medium permeability | about 500–1000 |
| high permeability | about 1000–2000 |
| very high permeability | more than about 2000 |

As noted above, materials with medium breathability, that is materials with MVTR values greater than about 500 g/m$^2$/24 h begin to be effective in allowing transport of moisture vapor from the void space between a wearer's body and an absorbent article.

Alternatively, such backsheets can comprise nonwoven materials, which have been made liquid impermeable such as by either minimizing the non-woven pore size e.g. by combining spunbonded webs with meltblown layers (SMS) or by other treatments. Such materials often have high or very high MVTR values, such as about 3000 g/m$^2$/24 h to 6000 g/m$^2$/24 h for non-woven webs, such that they also can be meaningfully described by an air permeability value (see TEST METHODS). For example, air permeabilities of between about 1500 to 2500 l/cm$^2$/sec result for conventional SMS materials, 2000 to 2300 l/cm$^2$/sec for common carded webs and greater than 2500 l/cm$^2$/sec for low basis weight spunbonded webs. The backsheet may have two or more zones, at least a first zone having a mass MVTR value of at least about 1300 g/24 h/m$^2$ and one or more of the remaining zones has a MVTR value greater than said MVTR value of the first zone.

Absorbent articles of the present invention, such as diaper 20 shown in FIG. 1, may also comprise zones having differing vapor or air permeabilities. For example, the chassis region 69 may be provided with high or very high permeability in order to maximize ventilation of the absorbent article while providing the central region 68 with a lower permeability in order to minimize the risk of leakage. As is discussed in greater detail below, the improved cores of the present invention widen the range of possible permeabilities in any region because of their improved rewet properties.

In addition to having satisfactory vapor or air permeability a material suitable for use as a backsheet 26 of the present invention must have sufficient liquid impermeability. Thus, in conventional diaper designs, using conventional materials, core region backsheet materials are substantially liquid impermeable. For purposes of the present invention, a material is considered to be impermeable if, as measured using the hydrostatic head test described in the TEST METHODS section below, the material is capable of resisting a water height of at least about 120 mm. Preferably, such materials are capable of resisting a water height of at least about 140 mm.

Treated Topsheet

A preferred means of providing a treated article that has a body contacting surface that provides a skin care benefit is to provide a topsheet. For example such a topsheet can be treated with a skin care composition that is either disposed on the body contacting surface thereof or can be delivered to the body contacting surface so as to provide the skin care benefit. For purposes of the present description, such a topsheet is described in terms of a topsheet that has been treated with a lotion composition which provides overhydration protection. One of skilled in the art will recognize that other skin care compositions could also be applied to some portion of an absorbent article which could then become available on a body contacting surface thereof so that effective amounts of the skin care composition could transfer to a wearer's skin and that such absorbent articles are also within the scope of the present invention.

Treated Topsheet: Topsheet Substrate Material

The topsheet 24 is preferably compliant, soft feeling, and non-irritating to the wearer's skin. Further, the topsheet 24 is liquid pervious, permitting liquids (e.g., menses and/or urine) to readily penetrate through its thickness. A suitable topsheet 24 may be manufactured from a wide range of materials such as woven and nonwoven materials (e.g., a nonwoven web of fibers); polymeric materials such 30 apertured formed thermoplastic films, apertured plastic films, and hydroformer thermoplastic films; porous foams; reticulated foams; reticulated thermoplastic films; and thermoplastic scrims. Suitable woven and nonwoven materials can be comprise of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroapertured, hydroentangled, combinations of the above, or the like. Such nonwoven webs may be bonded using means known to the art, such as chemical bonding, latex bonding, thermal bonding, and the like.

The topsheet 24 of the present invention may comprise a single layer as is shown in FIG. 1 or it may comprise more than one layer or material. For example, structures wherein the portion of the topsheet lying in the central region 68 may comprise a first material and the portion of the topsheet 24 that lies in the chassis region 69 may comprise a second material. Alternatively, the topsheet 24 may comprise a compound topsheet having more than one layer wherein a secondary topsheet underlies a primary topsheet. While none of these alternative topsheet structures is shown herein, one of skill in the art will recognize that these, and similar structures, all lie with in the scope of the present invention as long as the body contacting surface of at least a portion of the topsheet 24 is provided with (either by deposition thereon or migration thereto) a skin care composition that can transfer to a wearer's skin to provide a benefit, such as overhydration protection, thereto.

A topsheet 24 material which is particularly suitable for use in the diaper 20, is a carded nonwoven that is thermally bonded by means well known to those skilled in the fabrics art. A satisfactory material for the topsheet 24 of the present invention comprises staple length polypropylene fibers having a denier of about 2.2 As used herein, the term "staple length fibers" refers to those fibers having a length of at least about 15.9 mm (0.625 inches). Preferably, the material has a basis weight from about 14 to about 25 grams per square meter. A suitable material is manufactured by Veratec, Inc., a Division of International Paper Company, of Walpole, Mass. under the designation P-8.

The topsheet 24 of diaper 20 is preferably made using a hydrophilic substrate to promote rapid transfer of bodily fluids (e.g., urine) through the topsheet 24. If the material is hydrophobic, at least the upper surface of the topsheet 24 is treated to be hydrophilic so that liquids will transfer therethrough more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 which issued to Reising, et al on Jan. 29, 1991 and U.S. Pat. No. 4,988,345 which issued to Reising on Jan. 29, 1991, the disclosure of each of which is incorporated by reference herein.

Treated Topsheet: Skin Care Composition

While the specific composition(s) delivered (referred to herein as "skin care composition" and "composition") in accordance with the present method is not the critical factor in achieving maintained skin condition of the diapered area, it is apparent that the composition must provide either a protective, nonocclusive, function (e.g., a relatively liquid impervious but vapor pervious barrier) to protect against skin overhydration and skin exposure to materials contained in body exudates, or it must contain agents known for delivering, either directly or indirectly skin care benefits. The composition may be in a variety of forms, including, but not limited to, emulsions, lotions, creams, ointments, salves, powders, suspensions, encapsulations, gels, and the like.

As used herein, the term "effective amount of a skin care composition" referral to an amount of a particular composition which, when applied to or migratable to the body contacting surface of an absorbent article, will be effective in providing a protective barrier and/or delivering a skin care benefit when delivered via such absorbent articles over time. Of course, the effective amount of composition applied to the article will depend, to a large extent, on the particular composition used. Nonetheless, the quantity of the composition on a least a portion of the body contacting surface of the absorbent article will preferably range from about 0.05 mg/in$^2$ (0.01 mg/cm$^2$) to about 80 mg/in$^2$ (12 mg/cm$^2$), more preferably from about 1 mg/in$^2$ (0.15 mg/cm$^2$) to about 40 mg/in$^2$ (6 mg/cm$^2$), still more preferably 4 mg/in$^2$ (0.6 mg/cm$^2$) to about 26 mg/in$^2$ (4 mg/cm$^2$). These ranges are by way of illustration only and the skilled artisan will recognize that the nature of the composition dictate the level that must be applied to achieve the desired skin benefits, and that such levels are ascertainable by routine experimentation in light of the present disclosure.

While the level of skin care composition applied to the absorbent article is an important aspect of the present inventions, more important is the amount of composition transferred to the wearer's skin during use of one or more treated articles. Though the requisite level delivered to the skin to provide the desired skin benefits will depend to some degree on the nature of the composition employed, Applicants have found that relatively low levels may be delivered while still providing the desired skin effects. This is particularly true for preferred compositions, such as that described in Example 3. Another benefit of the present invention is the controlled application of the skin care composition to deliver the low levels of composition required. This is in contrast to typical, sporadic manual application of skin care agents, where the caregiver/user often applies significantly greater levels of material than are needed. Indeed, for certain materials, such as petrolatum, the levels applied manually may actually result in an occlusive effect, thereby compromising skin. Excessive materials added manually may also adversely impact the fluid handling properties of the absorbent article, as a result of transfer from the skin to the article. Thus, the present inventions, which allow controlled composition delivery throughout the wear period, allow delivery of optimal levels of the composition to the skin to maintain or improve skin health.

The method for determining the amount of skin care composition transferred to a wearer's skin after wearing one or more treated articles is described in the TEST METHODS section below. With regard to the level of skin care composition that is transferred to the wearer during use of one treated absorbent article worn for a period of about 3 hours (a typical daytime wear time), particularly for the preferred lotion composition of Example 3, preferred is where at least about 0.01 mg/in$^2$ (0.002 mg/cm$^2$), more preferably at least about 0.05 mg/in$^2$ (0.007 mg/cm$^2$), still more preferably at least about 0.1 mg/in$^2$ (0.015 mg/cm$^2$), of the composition is transferred to the skin over a three hour period. Typically, the amount of composition delivered by one treated article will be from about 0.01 mg/in$^2$ (0.002 mg/cm$^2$) to about 5 mg/in$^2$ (0.8 mg/cm$^2$), more preferably from about 0.05 mg/in$^2$ (0.007 mg/cm$^2$) to about 3 mg/in$^2$ (0.5 mg/cm$^2$), still more preferably from about 0.1 mg/in$^2$ (0.015 mg/cm$^2$) to about 2 mg/in$^2$ (0.3 mg$^2$). For example, the particularly preferred skin care composition described in Example 3 begins to provide a skin care benefit (i.e. begins to become effective against overhydration) at a transfer level of about 0.5 mg/in$^2$ (0.07 mg/cm$^2$).

For continual use of treated articles (in other words, changes occur in accordance with normal use patterns, which typically include changes every 3 to 4 hours during the day and a fresh article before overnight sleep) such as for a period of 24 hours, it will be preferred that at least about 0.03 mg/in$^2$ (0.004 mg/cm$^2$), more preferably at least about 0.1 mg/in$^2$ (0.015 mg/cm$^2$), still more preferably at least about 0.3 mg/in$^2$ (0.5 mg/cm$^2$), of the composition is transferred to the wearer's skin over the 24 hour period. Typically, the amount of composition delivered after a period of 24 hours where treated articles are applied at each change, will be from about 0.03 mg/in$^2$ (0.004 mg/cm$^2$) to about 18 mg/in$^2$ (2.8 mg/cm$^2$), more typically from about 0.1 mg/in$^2$ (0.015 mg/cm$^2$) to about 10 mg/in$^2$ (1.5 mg/cm$^2$), still more typically from about 0.3 mg/in$^2$ (0.04 mg/cm$^2$) to about 6 mg/cm$^2$ (0.9 mg/cm$^2$).

It will be recognized that of the numerous materials useful in the skin care compositions delivered to skin in accordance with the present methods, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 C.F.R. § 347), which presently include: alantoin, aluminum hydroxide gel, calamine, cocoa butter, dirnethicone, cod liver oil (in combination), glycerin, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use (21 C.F.R. § 347), which presently include: live yeast cell derivatives, aldioxa, aluminum acetate, microporous cellulose, cholecalciferol, colloidal oatmeal, cysteine hydrochloride, dexpanthanol, Peruvean balsam oil, protein hydrolysates, racemic methionine, sodium bicarbonate, Vitamin A, and the like.

Many of the FDA monographed skin care ingredients are currently utilized in commercially available skin care products, such as A+D® Ointment, Vaselinerdrzl Petroleum Jelly, Desitin® Diaper Rash Ointment, Gold Bond® Medicated Baby Powder, Aquaphor® Healing Ointment, Baby Magic® Baby Lotion, Johnson's UrltrJiL Sensitive® Baby Cream. These commercial products may be used in the treated articles of the present invention, either with or without modification to facilitate delivery thereof or to optimize such commercial product for use with an absorbent article (e.g. modify the rheology of such commercial products so as to minimize spreading thereof on or into an absorbent article).

As will be discussed hereinafter, the skin care compositions useful in the methods of the present invention preferably, though not necessarily, have a melting profile such that they are relatively immobile and localized on the body contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's body contacting surface, relatively low levels of composition are needed to impart the desired skin care benefits. In addition, special barrier or wrapping materials may be unnecessary in packaging the treated articles of the present invention.

In a preferred embodiment, for example, the lotion composition of Example 3, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components. Preferably, the lotion compositions of the present invention have a zero shear viscosity between about $1.0 \times 10^6$ centipoise and about $1.0 \times 10^8$ centipoise. More preferably, the zero shear viscosity is between about $5.0 \times 10^6$ centipoise and about $5.0 \times 10^7$ centipoise. The preferred lotion composition of Example 3 has a zero shear viscosity of about $1.0 \times 10^7$ centipoise. As used herein the term "zero shear viscosity" refers to a viscosity measured at very low shear rates (1.0 inverse seconds) using a plate and cone viscometer (a suitable instrument is available from TA Instruments of New Castle, Del. as model number CSL 100). One of skill in the art would recognize that using means other than high melting point components (as are discussed below) can be used to provide comparable viscosities and that the definition of zero shear viscosity would relate to a viscosity measured for such compositions measured by extrapolating a plot of viscosity vs. shear rate for such compositions to a shear rate of zero at a temperature of about 20° C.

Preferred compositions are at least semi-solid at room temperature to minimize composition migration. In addition, the compositions preferably have a final melting point (100% liquid) above potential "stressful" storage conditions that can be greater than 45° C. (e.g., warehouse in Arizona, car trunk in Florida, etc.). Representative compositions having these melt characteristics are described in detail in U.S. Pat. No. 5,643,588 (Roe et al.), U.S. Pat. No. 5,607,760 (Roe et al.), U.S. Pat. Nos. 5,609,587, and 5,635,191, the disclosure of each of which is incorporated herein by reference. Specifically, preferred compositions will have the following melt profile shown in Table 2:

TABLE 2

| Characteristic | Preferred Range | Most Preferred |
| --- | --- | --- |
| % liquid at room temp. (20° C.) | 2–50 | 3–25 |
| % liquid at body temp. (37° C.) | 25–95 | 30–90 |
| final melting point (° C.) | $\geq 38$ | $\geq 45$ |

By being solid or semisolid at ambient temperatures, preferred compositions do not have a tendency to flow and migrate to a significant degree to undesired locations of the article to which they are applied. This means less skin care composition is required for imparting desirable therapeutic or protective coating benefits.

While lotions having a melting point greater than the temperatures typically encountered in "stressful" environments is one means of providing the desired high zero shear viscosity, other means are also suitable. For example, The lotion could be provided with a structure which has a high zero shear viscosity but, on title application of shear, such structure collapses with a resulting viscosity reduction. Such structures can be provided by certain clay materials, such as bentonite clays or montmorillonite clays, and by fumed silica. Particularly preferred are the fume silicas as are available from the Cabot corp., Cab-O-Sil Div. of Tuscola, Ill. as Cab-O-Sil.

To enhance immobility of preferred compositions, the viscosity of the formulated compositions should be as high as possible to prevent flow to undesirable locations on or within the article. Unfortunately, in some instances, higher viscosities may inhibit transfer of composition to the wearers skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, and still more preferably from about 5 to about 100 centipoise as measured at 60° C. using, a rotational viscometer (a suitable viscometer is available from Lab Line Instruments, Inc. of Merlrose Park, Ill. as Model 4537). The viscometer is operated at 60 rpm using a number 2 spindle. As noted above, the zero shear viscosity of the lotion of the present invention is preferably between about $1.0 \times 10^6$ centipoise and about $1.0 \times 10^8$ centipoise. More preferably, the zero shear viscosity is between about $5.0 \times 10^6$ centipoise and about $5.0 \times 10^7$ centipoise.

For compositions designed to provide a therapeutic and/or skin protective benefit, a useful active ingredient in these compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. (It will be recognized that several of the monographed actives listed above are "emollients", as that term is used herein.) In a preferred embodiment, these emollients will have either a plastic or liquid consistency at ambient temperatures, i.e., 20° C. This particular emollient consistency allows the composition to impart a soft, lubricious, lotion-like feel.

Representative emollients useful in the present invention include, but are not limited to, emollients that are: petroleum-based; sucrose fatty acid esters; fatty acid ester type; alkyl ethoxylate type; fatty acid ester ethoxylates; fatty alcohol type; polysiloxane type; propylene glycol and derivatives thereof, polyethylene glycol and derivatives thereof, glycerin and derivatives thereof, including glyceride, acetoglycerides, and ethoxylated glycerides of $C_{12}$–$C_{28}$ fatty acids; triethylene glycol and derivatives thereof, spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; humectants; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

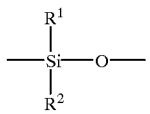

wherein, $R^1$ and $R^2$, for each independent siloxane monomeric unit can each independently be hydrogen or any alkyl, aryl, alkenyl, alkaryl arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silanes functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the diaper topsheet. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the diaper topsheets by such methods as, for example, emulsifying the polysiloxane in surfactant or providing the polysiloxane in solution with the aid of a solvent, such as hexane, listed for exemplary purposes only. Particular methods for applying polysiloxane emollients to diaper topsheets are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable humectants include but are not limited to: glycerin, propylene glycol, sorbitol, trihydroxy stearin, and the like.

When present, the amount of emollient that can be included in the composition will depend on a variety of factors, including the particular emollient involved, the lotion-like benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, preferred component of the therapeutic/skin protective compositions useful in the present invention is an agent capable of immobilizing the composition (including the preferred emollient or other skin condition, protective, or therapeutic agents) in the desired location in or on the treated article. Because certain of the preferred emollients in the composition have a plastic or liquid consistency at 20° C., they tend to flow or migrate, even when subjected to modest shear. When applied to a body contacting surface or other location of an absorbent article, especially in a melted or molten state, the emollient will not remain primarily in or on the treated region. Instead, the emollient will tend to migrate and flow into undesired regions of the article. Specifically, if the emollient migrates into the interior of the article, it can cause undesired effects on the absorbency of the article core due to the hydrophobic characteristics of many of the emollients and other skin conditioning agents used in the compositions useful in the methods of the present invention.

This migration of the emollient into the interior of the article can cause undesired effects on the absorbency of the article core due to the hydrophobic characteristics of many of the emollients and other skin conditioning agents used in the compositions useful in the present invention. It also means that much more emollient has to be applied to the article to get the desired therapeutic or protective benefits. Increasing the level of emollient not only increases the cost, but also exacerbates the undesirable effect on the absorbency of the article's core and undesired transfer of composition during processing converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solublized in the emollient with the aid of an appropriate emulsifier, or dispersed in the emollient), it entraps the emollient on the surface of the article's body contacting surface or in the region to which it is applied.

It is also advantageous to "lock" the immobilizing agent on the body contacting surface or the region of the article to which it is applied. This can be accomplished by using immobilizing agents which quickly "set up" (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the preferred properties of the skin care composition provide the skin benefits described herein. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behnyl alcohol, and mixtures thereof. The linear nature of these materials can speed up solidification on the surface of or within a treated article. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

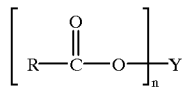

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof, Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid, sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides for use in the present invention will have the formula:

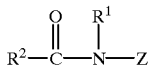

wherein $R^1$ is H, $C_1$–$C_4$ hydrocarbyl, 2-hydroxyethyl, 2-hydroxypropyl, methoxyethyl, methoxypropyl or a mixture thereof preferably $C_1$–$C_4$ alkyl, methoxyethyl or methoxypropyl, more preferably $C_1$ or $C_2$ alkyl or methoxypropyl, most preferably $C_1$ allyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars included glucose, fructose, maltose, lactose, galactose, mannose, and xylose. High dextrosie corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$[—$CH_2OH$, —$CH_2OH$—$CH_2$—$(CHOH)_2(CHOR^3)(CHOH)$—$CH_2OH$, where n is an integer from 3 to 5, and $R^3$ is for or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl $R^2$ can be selected to provide, for example, cocamides, stearamides, oleamidie, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxyrmaltotriotityl, etc.

The most preferred polyhydroxy fatty acid amides have the general formula:

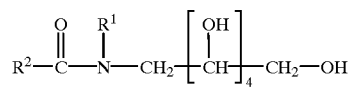

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozeokerite, beeswax, candelilla, paraffin, isoparaffin, ceresin, esparto, ouricuri, rezowax, and other known mixed and mineral waxes. The high melting point of these materials can help immobilize the composition on the desired surface of or location in the absorbent article. In addition, microcrystalline waxes are effective immobilizing agents either alone or in combination with other immobilizing agents. Microcrystalline waxes can also aid in "locking up" low molecular weight hydrocarbon materials within the skin care composition. A preferred alternative immobilizing agent is a paraffin wax, such as Parrafin S.P. 434, which is available from Strahl and Pitsch Inc., West Babylon, N.Y. 11704.

The amount of the optional inrumobriliing agent that can be included in the composition will depend on a variety of factors, including the actives (e.g., emollients) involved, the particular immobilizing agent involved, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

Of course, it is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care composition may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-topsheet rather than a being drawn through the topsheet and being absorbed by the absorbent core. Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB: values of at least about 7 and are sufficiently wettable without the addition of hydrophilic surfactant. Other immobilizing agents such as the $C_{16}$–$C_{18}$ fatty alcohols having HLB values below about 7 will require addition of hydrophilic surfactant to improve wettability when the composition is applied to article topsheets. Sirmnilarly, a hydrophobic emollient such as petrolatum will require the addition of a hydrophilic surfactant if hydrophilic composition is desired. Of course, the concern around wettability is not a factor when the body contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form homogeneous mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions tissue laminate tensile strength, adhesive bond sufficiencies, and the like.

Suitable nonionic surfactants may be substantially non-migratory after the composition is applied to the article topsheets and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30"° C. In this regard, these nonionic surfactants will preferably have melting points similar to those of the immobilizing agents previously described.

Suitable nonionic surfactants for use in compositions that will be applied to the topsheet of articles, at least in the liquid discharge region of the diaper, include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The allyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol, (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also, function as alkyl ethoxylate emollients). Other examples of preferred ethoxylated alcohol surfactants include ICI's class of Brij surfactants and mixtures thereorf with Brij 72 (i.e., Steareth-2) and Brij 76 (i.e., Steareth-10) being especially preferred Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Compositions can comprise other components typically present in emulsions, creams, ointments, lotions, powders, suspensions, etc. of this type. These components include water, viscosity modifiers, perfumes, disinfectant antibacterial actives, antiviral agents, pharmaceutical actives, film formers, deodorants, opacifiers, astringents, solvents, preservatives, vitamins, and the like. In particular, if a water based skin care composition is used, a preservative would be needed. Suitable preservatives include, but are not limited to: propylparaben, methylparaben, benzyl alcohol, benzalkonium chloride, tribasic calcium phosphate, butylated hydroxy toluene, or acids, such as citric, tartaric, malic, maleic, lactic, benzoic, salicylic, and the like.

Suitable viscosity modifiers include: some of the items also described as effective immobilizing agents, alkyl galactomannen, silica, talc sesquioleate, modified celluloses, such as hydroxyethyl cellulose, magnesium aluminum silicate, zinc stearate, and other viscosity modifiers as may be known to the art.

Suitable solvents include: propylene glycol, glycerin, cyclomethicone, polyethylene glycols, hexalene glycol, diol and multi hydroxy based solvents.

Suitable vitamins include vitamins: A, D3, E, and E acetate.

In addition, stabilizers can be added to enhance the shelf life of the composition such as cellulose derivatives, proteins and lecithin. All of these materials are well known in the art as additives for such formulations and can be employed in appropriate amounts in the compositions for use herein.

A particularly preferred skin care composition is the lotion composition discussed in Example 3 and described in Table 4. As is discussed below, this composition has been found to be particularly effective, when used in conjunction with the structures of the present invention in mitigating skin overhydration.

Preparing the Lotion and Treating Diaper Topsheets with the Lotion Composition

The particularly preferred lotion composition of the present invention can be prepared by melting the individual components thereof followed by simple mixing. The details of such preparation are given in Example 3 below.

In preparing absorbent articles of the present invention, the skin care composition is applied such that during wear, at least some portion of the composition will transfer from the treated article to the wearer's skin. That is, skin care composition is either applied directly to one or more wearer contacting surfaces, or is applied to alternate locations or means such that the skin care composition is readily available for transfer from one or more wearer contacting surfaces during use without intervention by the user/caregiver. (For example, materials positioned beneath the wearer contacting surface, encapsulated compositions, etc.) Of course, to effectuate delivery of composition to those body regions most susceptible to skin disorders, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc.

One preferred means of preparing a treated article according to the present invention is to apply the preferred lotion composition of Example 3 to the inner surface (i.e., the body facing surface) of a diaper topsheet substrate. Any of a variety of application methods that evenly distribute lubricious materials having a having a molten or liquid consistency can be used. Suitable methods include spraying, printing (e.g., flexographic printing), coating (e.g., gravure coating), slot extrusion, or combinations of these application techniques, e.g. spraying the lotion composition on a rotating surface, such as an application roll, that then transfers the composition to the outer surface of the diaper topsheet. The composition can be applied to the article at any point during assembly. For example, the composition can be applied to the finished disposable absorbent product before it has been packaged. The composition can also be applied to a given component (e.g., topsheet, cuffs, sides, waists, etc.), at the converting site or by the material supplier, before it is combined with the other raw materials to form a finished disposable absorbent product. Again, the composition can be applied to other zones of the article such that the composition will migrate to one or more wearer contacting surfaces during use.

The minimum level of composition to be applied to the article's wearer-contacting surface is an amount effective for providing the therapeutic and/or protective benefits when the composition is delivered pursuant to the present methods. The level of composition applied will depend on various factors, including the article component treated, the relative amount of surface area of the wearer-contacting surface not treated with the composition, the composition's content and the like. In general, with compositions that are relatively hydrophobic and are to be applied to essentially all of the topsheet, the composition is preferably applied to the article topsheet in an amount ranging from about 0.1 mg/in$^2$ (0.02 mg/cm$^2$) to about 15 mg/in$^2$ (2.3 mg/cm$^2$), more preferably from about 1 mg/in$^2$ (0.2 mg/cm$^2$) to about 10 mg/in$^2$ (2 mg/cm$^2$). It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

The composition can be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article.

In the case of a diaper topsheet, the manner of applying the lotion composition to the diaper topsheet should be such that the topsheet does not become saturated with the lotion composition. If the topsheet becomes saturated with the lotion composition, there is a greater potential for the lotion to block the topsheet openings, reducing the ability of the topsheet to transmit fluid to the underlying absorbent core. Also, saturation of the topsheet is not required to obtain the therapeutic and/or protective lotion benefits. Particularly suitable application methods will apply the lotion composition primarily to the outer surface of the diaper topsheet. A preferred application method is slot extrusion of the melted lotion onto that portion of the topsheet 24 that lies in central region 68 wherein the region of application is symmetrically disposed about the longitudinal centerline 67 and the lateral centerline 66. Particularly preferred is to apply such lotion in a plurality of spaced apart stripes (i.e. nonuniform coverage) so as to minimize the effect of the lotion on the absorbency properties of the diaper 20. Such particularly preferred application provides the central region 68 with open area so as to easily absorb bodily fluids as may be deposited thereon. As used herein, the "percent open area" of the topsheet 24 is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. It is understood that the crotch point is determined by placing the absorbent article on a wearer in the intended manner and determining where the crossed filament would contact the article. The length of the crotch region of an incontinence device (e.g. diapers or adult incontinent articles) typically corresponds to about 40% of the absorbent article's total length (i.e., in the y-dimension). With regards to sanitary napkins the length of the crotch region corresponds to about 80% of the articles's total length. The width of the crotch region is equivalent to the width of the widest absorbent core component as measured at the crotch point. As used herein, "untreated" means a region of the topsheet having less than about 0.05 mg/in$^2$ (0.1 g/in$^2$). In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired lotion effect and the desired fluid handling properties of the topsheet will be dictated largely by the characteristics of the lotion (in particular the lotion's composition and its relative hydrophobicity/hydrophilicity properties). One skilled in the art will appreciate that the desired percent open area will be readily determined through routine experimentation.

Surprisingly, while the topsheet or other regions comprising the composition is preferably treated nonuniformly (e.g., microscopic or macroscopic regions where no composition is applied), during wear of the article, the composition is transferred to the wearer even in regions of the skin corresponding to untreated regions of the topsheet. The amount and uniformity of composition transferred to the skin is believed to depend on several factors, including, for example, contact of the wearer's skin to the treated article surface, friction created during wear time between the wearer's skin and the treated region, warmth generated from wearer to enhance the transfer of the composition, the composition's properties, the materials which constitute the composition, and the like.

The lotion composition is typically applied from a melt thereof to the a substrate to form topsheet 24. Since the preferred lotion composition melts at a temperature significantly above ambient temperatures, it is usually applied as a heated coating to the topsheet. Typically, the lotion composition is heated to a temperature in the range from about 35° to about 100° C., preferably from 40° to about 90° C., prior to being applied to the diaper topsheet. Once the melted lotion composition has been applied to the diaper topsheet, it is allowed to cool and solidify to form solidified coating or film on the surface of the topsheet. The application process may also include unit operations designed to aid in the cooling/set up of the lotion. Such unit operations include, but are not limited to, external cooling of the treated article using blowers, fans, etc., chill rolls, and other such means as may be known to the art.

The minimum level of lotion to be applied to the diaper topsheets is an amount effective for reducing wearer skin overhydration. The lotion composition is preferably applied to a substrate to form topsheet 24 of the present invention in an amount ranging from about 0.05 mg/in$^2$ (0.1 g/m$^2$) to about 80 mg/in$^2$ (125 g/m$^2$) more preferably from about 1 mg/in$^2$ (2 g/m$^2$) to about 40 mg/in$^2$ (62 g/m$^2$), still more preferably from about 4 mg/in$^2$ (6 g/m$^2$) to about 26 mg/in$^2$ (40 g/m$^2$). Because the emollient is substantially immobilized, less lotion of the composition is needed to impart the desired skin care benefits. Such relatively low application levels of the lotion composition are adequate to impart the desired therapeutic and/or protective lotion benefits to the topsheet, yet do not negatively affect the absorbency and/or wettability properties of the topsheet. Lotion application is discussed in greater detail in copending U.S. patent application Ser. No. 08/908,852, entitled Article Having A Lotioned Topsheet, by Roe et al., filed on Aug. 8, 1997, the disclosure of which is incorporated herein by reference.

Regions of the Absorbent Article

However, apart from the selection the appropgriate materials, the arrangement of the materials within the absorbent article 20 is of high importance. For the scope of the following description, the absorbent article 20 is considered to comprise two regions, namely one part of the article comprising the absorbent core 28 (i.e. central region 68), the other part comprising the remainder of the absorbent article 20.

Thus, the central region 68 describes the region which will, in use, cover the body opening(s) from which bodily exudates are discharged, and will further longitudinally extend to a wearer's waist.

Apart from liquid handling means and auxiliary means such as elements to maintain the various other elements together (e.g. adhesives), this central region 68 will comprise one or more materials which are intended to face towards the skin of the wearer during use, and which are generally referred to as topsheet materials, and one or more materials which are intended to cover the opposite surface of the article (i.e. the garment surface).

The chassis region 69 comprises those elements of the article intended to hold the article on the wearer (i.e. fixation means), the elements intended to prevent bodily exudates from leaking out of the article (e.g. elasticized leg cuffs 34, or the waist feature 34), and means to connect the various elements (e.g. fastening system 36).

The chassis region 69 also comprises one or more materials intended to face towards the skin of the wearer during use, and which is generally referred to as, topsheet 24, and one or more materials intended to cover the opposite surface of there article (i.e. the backsheet 26). As noted above, when using a breathable material for the backsheet 26 in such articles, the backsheet materials need to have maximum vapor breathability without allowing liquids to pass through.

Breathability and Treated Topsheet

In one aspect of the present invention the breathable backsheets 26 and the topsheets 24 cooperate to provide a skin care benefit (e. g. overhydration protection). While not being bound by theory, the Applicants believe the following provides an explanation of how this cooperation provides such a benefit.

The preferred skin care compositions of the present invention, as delivered by treating the topsheet 24 as described above, serve to provide a additional barrier to interaction between excess environmental moisture and a wearer's skin. In order to provide an effective barrier, at least a portion of the preferred skin care composition of the present invention, in the form of the lotion described below, must be transferred from the topsheet to a wearer's skin. The Applicants have found that transferring as little as 0.07 mg/cm$^2$ begins to become effective in reducing skin overhydration as, measured by in vivo testing (Example 4). Treated topsheets 24 having lotion levels in the preferred range discussed above are effective in transferring such effective amounts of the skin care composition of the present invention to a wearer after about six hours of wear time. (It should be recognized that the amount of time for transfer of an effective amount of a skin care composition depends on several factors, including the specific skin care composition, composition application level, wearer activity level, and the like.) The Applicants have also found further reductions in skin overhydration at lotion transfer levels of 0.17 mg/cm$^2$. Methods for determining transfer level and overhydration are described in the TEST METHODS section below and discussed in greater detail with the examples.

Excessive relative humidity in the void space between the wearer's skin and the absorbent article can interfere with the normal transport of water vapor into and out of the skin. By providing a means for transport of such excess moisture (breathable backsheet 26) the driving force toward overhydration is reduced. As noted above, backsheets having a MVTR value of as low as 500 g/24 h/m$^2$ begin to become effective in providing a means for excess relative humidity to be transported away from the void space between a wearer's skin and an absorbent article. Preferably, the MVTR of such a breathable backsheet 26 is at least about 900 g/24 h/m$^2$. More preferably, the MVTR of the breathable backsheet 26 is at least 1300 g/24 h/m$^2$.

As is clearly shown in Example 5, providing a breathable backsheet 26 reduces skin overhydration over and above the reduction provided by the skin care composition of the present invention alone. That is, the topsheet (skin care composition) and the breathable backsheet can co-operate to provide a meaningful skin care benefit.

Improved Core Performance and Treated Topsheet

Improved protection against skin overhydration can also be achieved by combining the improved cores 28 discussed above with the topsheet also discussed above. While not being bound by theory the following discussion may prove useful in understanding how such a combination can provide improved protection against skin overhydration. In simplified terms, the stratum corneum provides the primary barrier against overhydration of underlying layers of skin. As such, moisture in the stratum corneum and in underlying layers of skin is in equilibrium with environmental moisture. When the skin is occluded (e.g. by an absorbent article), the level of environmental moisture can change. For example, after urination, moisture that is absorbed by the absorbent article serves as a source of supply for additional environmental moisture that would not otherwise be present.

An absorbent article comprising the improved cores and the topsheet of the present invention can address such potential overhydration as follows:

If such environmental moisture is not closely held it can be redelivered to the skin due to wearer movement (rewet) and possibly cause skin overhydration. If such moisture cannot reach a wearer's skin the risk of overhydration is reduced. As noted above, the absorbent cores 28 of the present invention serve to hold absorbed bodily fluids more tightly (reduced rewet).

The skin care compositions of the present invention serve to provide a additional barrier to interaction between excess environmental moisture and a wearer's skin. In order to provide an effective barrier, at least a portion of the preferred skin care composition of the present invention, in the form of the lotion described below, must be transferred from the topsheet to a wearer's skin. The Applicants have found that transferring as little as 0.07 mg/cm$^2$ begins to become effective in reducing skin overhydration as measured by in vivo testing. Treated topsheets 24 having lotion levels in the preferred range discussed above are effective in transferring such effective amounts of the skin care composition of the present invention to a wearer after about six hours of wear time. (It should be recognized that the amount of time for transfer of an effective amount of a skin care composition depends on several factors, including the specific skin care composition, composition application level, wearer activity level, and the like.) The Applicants have also found further reductions in skin overhydration at lotion transfer levels of 0.17 mg/cm$^2$. Methods for determining transfer level and overhydration are described in the TEST METHODS section below and discussed in greater detail with the examples.

In other words, the improved absorbent cores 28 and the topsheet 24 cooperate to provide a skin care benefit to a wearer's diapered skin. Such a benefit is demonstrated by the results of Example 6.

Improved Core Performance and Breathability

The improved absorbent cores 28 discussed above, which have a high liquid retention capability (i.e. low rewet), when combined with the breathable backsheets 26 also discussed above can provide absorbent articles which improved protection against overhydration when compared to diapers of the present art. While not being bound by theory the following discussion may be useful in understanding the mechanism providing the improved protection. As noted above skin overhydration, when wearing an absorbent article such as a diaper, can be attributed to either:

the presence of aqueous bodily fluids on the skin which can macerate the skin causing overhydration.

or excessive relative humidity in the void space between the wearer's skin and the absorbent article which can interfere with the normal transport of water vapor into and out of the skin.

In either case, such occlusion can cause the wearer's skin to accumulate excessive water (i.e. become overhydrated). Absorbent articles of the present invention, such as diaper 20, can counteract this imbalance by providing means to keep excessive moisture off a wearer's skin (reduced rewet) and means to minimize excessive relative humidity in the void space between the wearer's skin and the absorbent article (breathability). Further, the improved cores of the present invention not only provide reduced rewet but also, because they store bodily fluids more efficiently, they are less likely to release such bodily fluids for transport through a breathable backsheet. As a result, backsheets having higher MVTR properties have suitable for use in absorbent articles. A single measure reflecting both of these important properties is the ratio of the PACORM value for an absorbent core to the MVTR value for a backsheet material. The ratio of PACORM value and MVTR. value should be minimized in order to provide absorbent articles with maximum breathability and minimum rewet. Such minimization can be achieved either by small PACORM values, and/or high MVTR values. For example, a diaper having an improved core of the present invention with a PACORM value of about 65 mg could be used in a diaper 20 of the present invention with a breathable backsheet 26 having a MVTR value of 1300 $g/m^2/24$ h. Such a diaper having a ratio of about 0.05 $mg/(g/m^2/24$ h) would be effective in reducing overhydration when compared to diapers of the current art. The Applicants have found that a PACORM:MVTR ratio of about 0.05 $mg/(g/m^2/24$ h) or less is effective. Preferably, the PACORM:MVTR ratio is less than about 0.04 $mg/(g/m^2/24$ h). More preferably, the ratio is less than about 0.03 $mg/(g/m^2/24$ h).

As noted above, the PACORM:MVTR ratio is a useful measure of the relationship between the absorbent core 28 and the breathable backsheet 26 of the present invention. This means, depending on the rewet properties (i.e. PACORM value) of a particular improved absorbent core 28, the MVTR of a breathable backsheet of the present invention can vary. Obviously, as MVTR increases cores 28 with greater rewet would still be suitable. Thus, for a backsheet 26 with a MVTR of about 1500 $g/m^2/24$ h, a core 28 could have a PACORM value of about 75 mg and still be suitable for use in the present invention. Similarly, the following combinations of backsheet MVTR and core PACORM value would all be suitable: 1800 $g/m^2/24$ h and 90 mg; 2000 $g/m^2/24$ h and 100 mg; and 2200 $g/m^2/24$ h and 110 mg.

Improved Core Performance, Breathability, and Treated Topsheet

Clearly, if any pair of the breathable backsheet 26 and treated topsheet 24, the improved core 28 and treated topsheet 24, or the improved core 28 and breathable backsheet 26 can cooperate to provide improved protection against overhydration, an absorbent article comprising all three components would also be expected to be effective against overhydration. Thus, a particularly preferred embodiment of the present invention comprises treated topsheet 24, the breathable backsheet 26, and the improved absorbent cores 28 each of which has been discussed above.

Such an absorbent article comprises elements that serve to mitigate all three of the major sources of skin overhydration.

That is:
Treating the topsheet 24 serves to provide an additional barrier to environmental moisture between a wearer's skin and the local environment as defined by the portion of the wearer's skin that is occluded by the absorbent article.

The breathable backsheet 26 serves to reduce moisture vapor in at least a portion of the void space between a wearer's body and the absorbent article.

The improved cores 28 provide reduced rewet which reduces environmental aqueous liquids within that portion of a wearer's body that is occluded by the absorbent article. Because the improved cores 28 retain aqueous liquids more tenaciously, they also enable the use of backsheet materials having greater breathability (see below).

A diaper embodiment of this particularly preferred absorbent article is shown as diaper 20 in FIG. 1. In this particularly preferred embodiment the topsheet 24 has been treated with a skin care composition as described above.

In alternative embodiments of the present invention (not shown) other diaper components can also transfer effective amounts of a skin care composition to a wearer's skin. For example, the elastic leg cuffs 32 discussed above, particularly the barrier cuff 84 or the gasketing cuff 104 thereof could be provided with the preferred skin care composition of the present invention for transfer to a wearer's skin. Similarly, the elastic waist feature 34 could also be provided with the skin care composition of the present invention for transfer to a wearer's skin. Providing such elements of an absorbent article with the skin care compositions of the present invention is particularly useful because, as noted above, overhydrated skin becomes macerated and, as a result, more susceptible to mechanical damage. Because the constrictive nature of the elastic leg cuffs 32 and the elastic waist feature 34 can cause such damage, providing means to ameliorate such overhydration, such as a lotion or the like, disposed on such elements wherein effective amounts of the lotion transfer to a wearer's skin, would reduce the degree of mechanical damage to the skin caused by such elements. Providing lotions of the type described herein to such elasticized elements has the further advantage of providing a lubricating means between such constricting elements and a wearer's skin. Articles having elasticized cuffs that are treated with a skin care composition of the type disclosed herein are disclosed in copending U.S. patent application Ser. No. 08/766,386, entitled Absorbent Articles Having Lotioned Leg Cuffs, by Schulte et. al., filed on Dec. 3, 1996, and in copending U.S. patent application Ser. No. 08/840, 039, entitled Absorbent Articles Having Lotioned Leg Cuffs Containing A Polysiloxane Emollient, by Schulte et. al., filed on Apr. 24, 1997, the disclosure of which is incorporated herein by reference.

While the preferred embodiment of the absorbent article of the present invention has been discussed in terms of a diaper, it will be recognized by one of skill in the art that other types or absorbent articles can also apply the structures taught herein and that the disclosure above is merely for illustrative purposes. In particular, the present invention is also suitable for application to incontinence articles, catamenial devices, and training pants.

Another disposable absorbent article for application of the structures of the present invention is incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. No. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992). The disclosure of each of these references is incorporated herein.

Also suitable for application of the structures of the present invention are catamenial devices, such as sanitary napkins. Suitable absorbent articles are disclosed in U.S. Pat. No. 4,556,146, issued to Swanson, et al. on Dec. 3, 1985, B14589876, issued to Van Tilberg on Apr. 27, 1993, U.S. Pat. No. 4,687,478, issued to Varn Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to van Tilburg on Dec. 7, 1993, U.S. Pat. No. 5,389,094, issued to Lavash, et al. on Feb. 14, 1995, U.S. Pat. No. 5,413,568, issued to Roach, et al. on May 9, 1995, U.S. Pat. No. 5,460,623, issued to Emenaker, et al. on Oct. 24, 1995, U.S. Pat. No. 5,489,283, issued to Van Tilburg on Feb. 6, 1996, U.S. Pat. No. 5,569,231, issued to Emenaker, et al. on Oct. 29, 1996, and U.S. Pat. No. 5,620,430, issued to Bamber on Apr. 15, 1997, the disclosure of each of which is incorporated herein reference.

The structures of the present invention may also be employed on training pants to provide skin condition benefits. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell, et al. on Oct. 29, 1996, U.S. Pat. No. 4,940,464, issued to Van Gompel, et al. on Jul. 10, 1990, and U.S. Pat. No. 5,092,861, issued to Nomura, et al. on Mar. 3, 1992. The disclosure of each of which is incorporated herein by reference.

The following examples serve to point out the particular benefits of various aspects of the present invention.

EXAMPLES

Example 1

Samples of different baby diapers have been evaluated using the various test methods listed in the TEST METHODS section below. For comparability reasons, all were of comparable size, namely of for babies of about 9 to 18 kg, often called SIZE 4.

A commercially available product, PAMPERS Baby Dry Plus MAXI/MAXI PLUS size as marketed by Procter & Gamble in Europe was prepared with the following modifications:

A) The core 28 was modified according to the present invention by the following steps:
1) Chemically treated stiffened cellulosic material as is supplied by Weyerhaeuser Co., Tacoma, Wash. under the trade designation of "CM" functioning as an acquisition/distribution layer 28b overlying the storage core 28c and having a basis weight of about 590 g/m$^2$.
2) An additional acquisition layer 28a is introduced between the topsheet 24 and the chemically treated stiffened cell loft chemically bonded nonwoven as supplied by PGI Nonwovens, Fibertech Group, Landisville, N.J. under the designation Type 6852 was used. This material is a chemically bonded PET fiber web having a basis weight of 42 g/m$^2$ and arwrvdth of 10 mm over the full length of the absorbent core.
3) The cellulose material usage in the storage core 28c which lies beneath the chemically treated stiffened cellulosic 28b material is reduced to about 11.5 g therein.
4) The amount of superabsorbent material in this storage core 28c is increased to about 16 g therein. The superabsorbent material was supplied by Stockhausen GmbH, Germany under the trade name FAVOR SXM type T5318.

This diaper, modified according to the improved core of the present invention, has a PACORM value of 72 mg.

Example 2

A similar diaper 20 having an absorbent core 28 as described in Example 1 can be prepared also having a backsheet 26 comprising a microporous film such as supplied by EXXON Chemical Co., Bay City, Tex. under the designation EXXAIRE. Such a microporous film has a MVTR value of about 4500 g/m$^2$/24 h. The ratio of PACORM to MVTR for such a diaper 20 is 0.016 mg/(g/m$^2$/24 h).

Table 3 compares this experimental diaper 20 with the following similar diapers:

Comparative diaper 1 contains the improved and modified core as in Example 1, but has a conventional, non breathable polyethylene backsheet material.

Comparative diaper 2 is similar to diaper 20 described above but comprises a very high permeability microporous backsheet, such as supplied by Mitsui Toatsu, Japan under the designation ESPOIR NO.

Comparative diaper 3 is a commercially available product as marketed by UniCharm Corp. in Japan under the trade designation MOONEYMAN, size 4. This product has a very high permeably microporous film covering both the core and the chassis regions

TABLE 3

| Product Tested | PACORM (mg) | MVTR (g/m$^2$/24 h) core | chassis | PACORM:MVTR Ratio (mg/(g/m$^2$/24 h) |
|---|---|---|---|---|
| Diaper of Example 2 | 72 | 4500 | 4500 | 0.016 |
| Comparative Diaper 1 | 72 | 200 | 200 | 0.36 |
| Comparative Diaper 2 | 72 | 3800 | 3800 | 0.019 |
| Comparative Diaper 3 | 180 | 3300 | 3300 | 0.054 |

Example 3

Experimental size 4 diapers, structurally equivalent to commercially available PAMPERS PREMIUM (Procter & Gamble, Cincinnati, Ohio) size 4 diapers, were prepared with a topsheet having the particularly preferred composition described in Table 4.

TABLE 4

Test Lotion Composition

| Component Description | Percent by Weight |
|---|---|
| Petrolatum[1] | 58 |
| Stearyl Alcohol[2] | 41 |
| Aloe Extract[3] | 1 |

[1]Available from Witco, Corp., Greenwich, CT as White Protopet ® IS
[2]Available from Procter & Gamble, Cincinnati, OH as CO1897
[3]Available from Madis Botanicals, Inc., South Hackensack, NJ as Veragel Lipoid As noted above, the components were mixed in the melt. The melted lotion was applied to the topsheet of the experimental diapers as 5 spaced apart stripes each stripe being 0.25 inches (0.6 cm)×11.75 inches (30 cm) at a lotion basis weight of 12 g/m² in the stripes.

Lotion transfer was measured after various wear times using the method described in the TEST METHODS section below. The results are given in Table 5.

TABLE 5

In vivo Lotion Transfer

| Wear Time | Amount of Lotion Transferred (mg/cm²) |
|---|---|
| 3 Hours | 0.05 |
| 6 Hours | 0.07 |
| 18 Hours | 0.10 |
| 24 Hours | 0.17 |

Example 4

This example compares the effect of lotion on skin hydration using the Skin Hydration Measurement Test described in the TEST METHODS section below.

Commercially available Pampers Premium (Size 4) diapers, available from Procter & Gamble, Cincinnati, Ohio were used to occlude subject forearms as described in the Skin Hydration Test. The preferred lotion described in Table 4 was applied to one forearm for each subject at one of two levels: approximately 0.07 mg/cm² or 0.17 mg/cm². The other forearm served as a non lotioned control.

The results of this experiment are given in Table 6. The effect on skin hydration is measured by the ratio of the area under the curve of TEWL data versus time (AUC) for the lotioned arm to the AUC for the non lotioned arm. The calculation for AUC is given in the TEST METHODS section. Normalized Integrated Vapor Flux values of less than 100% mean that the test condition is giving up water less rapidly (lower AUC) than the control, an indication of reduced overhydration.

TABLE 6

In vivo Effect of Lotion on Skin Hydration

| Amount of Lotion Applied (mg/cm²) | Normalized Integrated Vapor Flux (Percent of Unlotioned Control) | Change from Control (Percent) |
|---|---|---|
| None | 100 | 0 |
| 0.07 | 94 | 6 |
| 0.17 | 73 | 27 |

Similarly, the immediate effect of a treatment on skin surface moisture can be shown by comparing the to values for TEWL, where the $t_0$ value is determined as described in the TEST METHODS section below. Table 7 compares the ratio of such values for the products of Example 4. This analysis of the immediate effect shows the same benefit of the lotion of the present invention in reducing overhydration.

TABLE 7

In vivo Effect of Lotion on Skin Hydration

| Amount of Lotion Applied (mg/cm²) | $t_0$ TEWL (% Control) | Change from Control (Percent) |
|---|---|---|
| None | 100 | 0 |
| 0.07 | 92 | 8 |
| 0.17 | 74 | 26 |

As can be clearly seen in Tables 6 and 7, even at lotion levels of as low as 0.07 mg/cm² the preferred lotion of the present invention begins to become effective in reducing overhydration when compared to an unlotioned control.

Example 5

This example is similar to Example 4 with the exception that diapers having a breathable backsheet (MVTR=1300 g/24 h/m²)were compared to a control diaper having the same diaper structure without such a backsheet. The control diaper is available from Procter & Gamble, Cincinnati, Ohio as PAMPERS BABY DRY. The breathable backsheet is available from Clopay, corp., Cincinnati, Ohio as material number 97042501. The comparison was made at an applied lotion level of 0.17 mg/cm² using the preferred lotion described above in order to estimate the effect of breathability on skin hydration.

As can be seen in Tables 8 and 9, a breathable backsheet provided an additional benefit in reducing forearm skin hydration when compared to a non breathable backsheet.

TABLE 8

In vivo Effect of Lotion on Skin Hydration

| Backsheet MVTR (g/24 h/m²) | Normalized Integrated Vapor Flux (Percent of Unlotioned Control) | Change from Control (Percent) |
|---|---|---|
| ~200 | 100 | 0 |
| 1300 | 89 | 11 |

TABLE 9

In vivo Effect of Lotion on Skin Hydration

| Backsheet MVTR (g/24 h/m²) | $t_0$ TEWL (% Control) | Change from Control (Percent) |
|---|---|---|
| ~200 | 100 | 0 |
| 1300 | 81 | 19 |

While not being bound by theory, the Applicants believe that Table 9, in particular, shows the benefits of breathability because any effect due to relative humidity minimization would be most apparent shortly after removing the occlusive diaper.

Example 6

The following example is intended to demonstrate the cooperation between the improved cores of the present invention and the topsheet of the present invention.

The bottom collagen sheet 510 of the PACORM test (see TEST METHODS section and FIG. 3) was treated with the preferred lotion composition of the present invention to apply an amount of lotion in the range of transfer weights shown to be effective in vivo (~0.13 mg/cm$^2$). This lotion-modified collagen is intended to simulate the barrier effect of lotion transfer to a wearer's skin from wearing an absorbent article of the present invention. Lotion was applied to the bottom collagen sheet 510 by the following procedure:

1) Melt the lotion in a petri dish and allow to resolidify (cool to room temperature) so as to form a smooth surface.
2) Preweigh a collagen sheet 510 an place carefully onto the smooth lotion surface.
3) Using a petri dish with a smaller diameter than used to melt and resolidify the lotion, gently rub the collagen sheet 510 as it rests on the lotion surface.
4) Reweigh the collagen sheet 510 to determine lotion transfer.
5) Using the lotion-modified collagen sheet 510, conduct the) PACORM test: as described in the TEST METHODS section below.

PACORM values for each of the following diaper structures using the lotion-modified collagen are listed in Table 10.

TABLE 10

Lotion Barrier Effect on PACORM

| Condition | PACORM (mg/cm$^2$) |
|---|---|
| Current Art Diaper Core 1[1] | |
| No Lotion | 170 |
| 0.13 mg/cm$^2$ Lotion | 135 |
| Difference | 35 |
| Current Art Diaper Core 2[2] | |
| No Lotion | 185 |
| 0.12 mg/cm$^2$ Lotion | 121 |
| Difference | 64 |
| Improved Diaper Core[3] | |
| No Lotion | 65 |
| 0.13 mg/cm$^2$ Lotion | 24 |
| Difference | 41 |

[1]Available from Procter & Gamble Cincinnati, OH as PAMPERS PREMIUM
[2]Available from Kimberly Clark in Europe as HUGGIES
[3]Improved core 28 of the present invention as described in Example 1

As can be seen from the data in Table 10, both the improved diaper cores of the present invention (compare improved diaper core results to current art core results) and the lotion of the present invention (compare lotion/no lotion results for each core) clearly reduce transport of excess moisture into the skin analog of the PACORM test.

TEST METHODS

Moisture Vapor Transmission Rate

The Moisture Vapor Transmission Rate (MVTR) determines the amount of moisture adsorbed by calcium chloride in a "up" like container that is covered by a test specimen where the moisture source is a controlled temperature/humidity environment (40±3° C./75±3% relative humidity) separated from the calcium chloride by the test specimen.

The sample holding a cup is a cylinder with an inner diameter of 30 mm and an inside height from bottom to top flange of 49 mm. A flange having a circular opening to match the opening of the cylinder can be fixed by screws, and a silicone rubber sealing ring with an opening matching the inner diameter of the cup, fits between the top flange and the cylinder. The test specimen is positioned such that it covers the cylinder opening. The specimen is tightly fixed between the silicone rubber sealing and the upper flange of the cylinder so it acts as a barrier to moisture transport.

The equipment as well as the test specimen should be equilibrated to the temperature of the controlled environment prior to testing.

The absorbent desiccant material is $CaCl_2$, such as can be purchased from Wako Pure Chermical Industries Ltd., Richmond, Va. under the product designation 030-00525. If kept in a sealed bottle, it can be used directly. It also can be sieved to remove lumps, or excessive amounts of fines, if existing. It also can be dried at 200° C. for about 4 hours.

The $CaCl_2$ is weighed (15.0±0.02 g) into the cup, and tapped lightly so as to level it out, such that the surface is about 1 cm from the top of the cup.

A test sample, cut to about 3.2 cm by 6.25 cm, is placed flat and overlapping with the seal over the opening, and the seal and the top flange are affixed by the screws without over tightening. The total weight of the cup assembly is accurately recorded to four decimal places, and the assembly is placed into the constant temperature/humidity chamber.

After 5 hours exposure to the test humidity (without opening of chamber), the sample is removed and immediately covered tightly with a non-vapor permeable plastic film such as SARAN WRAP. After cooling about 30 minutes to allow for temperature equilibration, the plastic film is removed and the assembly is reweighed.

The MVTR value is then calculated by determining the moisture increase over 5 hours due to transport through the 3 cm circular opening and converting the result to units of "g24 h/mrz".

For each test, three replicates should be run, the resulting values will be averaged, and the result rounded to the nearest 100 value.

Overall, this method is applicable to thin films, multi layer laminates and that like. Experience has shown, that typical standard deviations range between 50 and 250 g/24 h/m$^2$ for averaged values of up to about 5000 g/24 h/m$^2$.

Air Permeability

The air permeability is determined by measuring the time in which a standard volume of air is drawn through the test specimen at a constant pressure and temperature. This test is particularly suited to materials having relatively high permeability to gases, such as nonwovens, apertured films and the like.

The test is operated in a temperature and humidity controlled environment, at 22±2° C. and 50±2% relative humidity. The test specimen has to be conditioned for at least 2 hours.

Suitable test equipment is manufactured by Hoppe & Schneider GmbH, Heidelberg, Germany, under the designation "Textiluhr nach Kretschmar". The apparatus is essentially a bellows in a vertical arrangement, with its upper end being mounted in a fixed position, and the lower end being releasably held at its upper position, which can be loosened by means of a release handle to slide under controlled conditions to the lower position, thereby increasing the volume inside the bellows by pulling air through the test specimen which covers the air inlet opening at the upper end of the bellows. The test specimen is firmly held to cover the air inlet opening by means of a fastening ring having an area of either 5 cm² or 10 cm² (allows for different samples sizes and/or different permeability ranges). If the 10 cm² ring is used, the sample should be at least 55 mm wide, for the 5 cm² ring a sample width of at least 35 mm is required. For both, the samples should have a length of about 150 mm.

Optionally, the sample holding device can comprise a stretching element, such as to enable measurement of elastic materials under stretched conditions.

The equipment comprises a stopwatch (1/100 sec increments) which automatically measures the time between the operation of the release handle, which starts the sliding of the bellows, and the bottom of the bellows reaching its lower or stop position.

The air permeability of the material can then be calculated by dividing a constant (provided by the supplier for each individual test apparatus; K is about 200.000 for a tested area of 5 cm², and about 400.000 for an area of 10 cm²) by the time as measured in seconds, resulting in units of: liters/cm²/sec.

The test is repeated once for each test sample, and should be repeated on 10 samples to provide a representative value for a material.

Hydrostatic Head

In this test an adjustable head of distilled water on the top side of a sample having an area of about 64 cm² is increased until visible water appears on the opposite side of the sample. The hydrostatic head where water first appears to transfer through the sample is recorded as the hydrostatic head for that sample.

A test specimen is cut to about 10 cm by 10 cm and placed over a sample plate having dimensions of about of 10 cm by 10 cm with a centered O-ring seal having a diameter of about 8 cm. The sample plate has a centered opening having a diameter of about 7.6 cm to allow observation of the bottom side of the sample during the test. The sample plate is carefully positioned under a 7.6 cm inner diameter Perspex column that is about 1 m tall, with a mounting flange so as to conveniently allow tightening of the sample plate carrying the sample underneath by means of screws. Optionally, a mirror may be positioned under the opening in the sample plate to ease the observation.

The cylinder has an sideways oriented opening with a diameter of about 1 cm to allow connection with a pump. The opening enters the column about 1 cm above where the sample is mounted. Optionally, a three-way-valve can be mounted in this connection to allow easier emptying of the column after the test.

The pump is set to raise the liquid head in the cylinder to a height of 25.4 cm within 60±2 seconds after the pump is turned on.

After starting of the pump the condition of the bottom surface of the test specimen is monitored. When the first drop falls off the test specimen, the pump is immediately stopped, and the height in the column is recorded in millimeters.

For each material, five tests should be repeated and the results should be averaged.

Acquisition Test

This test should be carried out at about 22±2° C. and at 35±15% relative humidity. The synthetic urine used in these test methods is commonly known as Jayco SynUrine and is available from Jayco Pharmaceuticals Company of Camp Hill, Pa. The formula for the synthetic urine is: 2.0 g/l of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$; and 0.23 g/l of $MgCl_2$. All of the chemicals are of reagent grade. The pH of the synthetic Urine is between bout 6.0 and 6.4.

Figure 3:
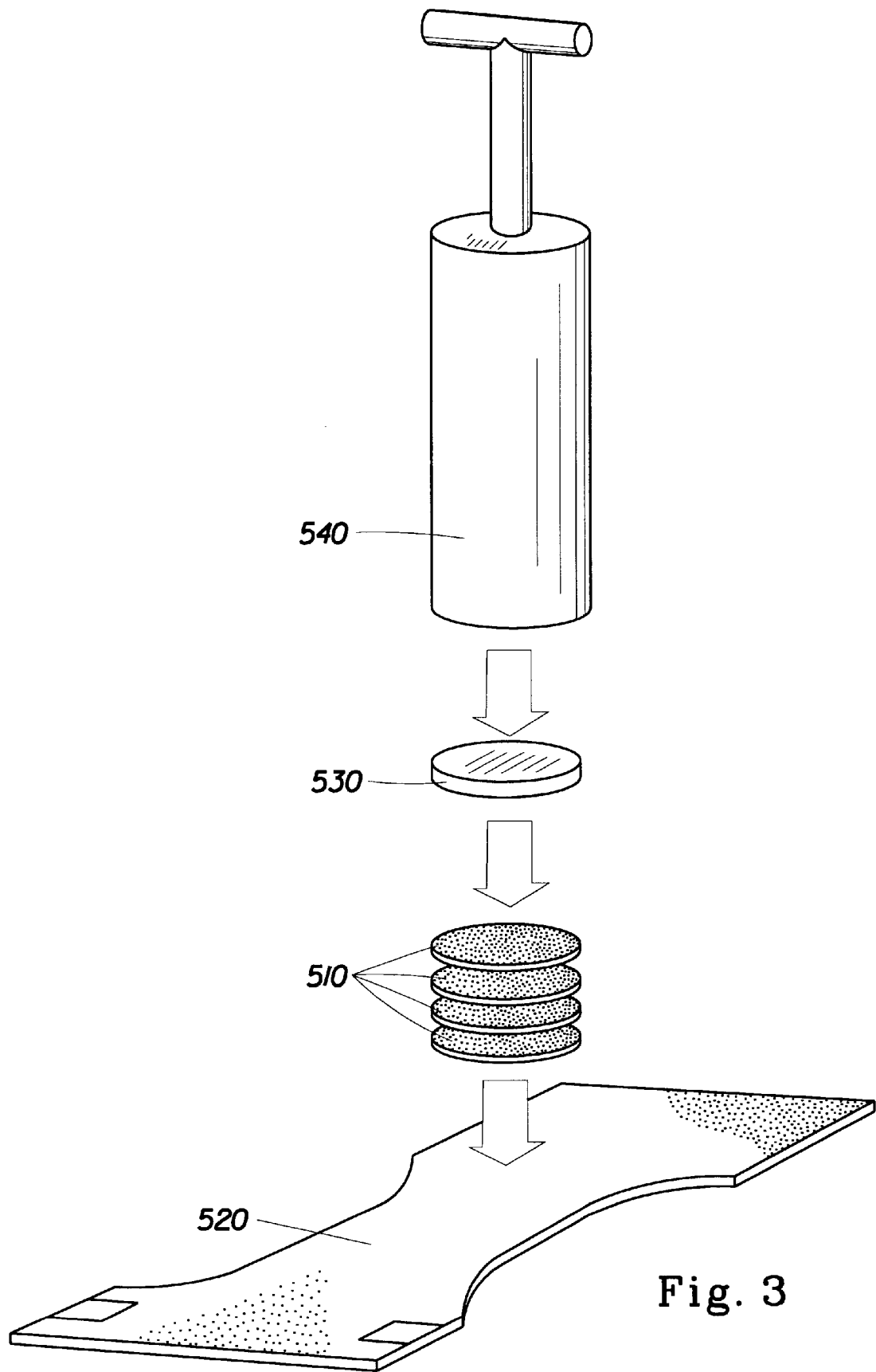
FIG. 3 is a schematic drawing showing the test set up for the Post Acquisition Collagen Rewet Method described in the TEST METHODS section.

Referring to FIG. 3, an absorbent structure (410) is loaded with a 75 ml gush, of synthetic urine at a rate of 15 ml/s using a pump (Model 7520-00, supplied by Cole Palmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 411 within a Perspex box (only base 412 of which is shown). A Perspex plate 413 having a 5 cm diameter opening in its middle is placed on top of the sample on the loading zone of the structure. Synthetic urine is introduced to the sample through a cylinder 414 fitted, and glued into the opening. Electrodes 415 are located on the lowest surface of the plate, in contact with the surface of the absorbent structure 410. The electrodes are connected to the timer. Loads 416 are placed on top of the plate to simulate, for example a baby's weight. A pressure of about 50 g cm-2 (0.7 psi) is achieved by positioning weights 416, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products or for smaller babies), the settings in particular of the fluid volume per gush should be adjusted appropriately to about 20% of the total article design capacity, and the deviation from the standard test protocol should be recorded.

Post Acquisition Collagen Rewet Method

Overview

The Post Acquisition Rewet Method (PACORM test) uses a material analogous to skin (collagen) to approximate the effect of rewet on skin. The test is shown diagrammatically in FIG. 5

Materials

Collagen Film Available form NATURIN GmbH, Weinhein, Germany, under the designation of COFFI. Film with a basis weight of about 28 g/m² is used.

Method

1) Cut the film into sheets with a diameter of 90 mm diameter (e.g. by using a sample cutter device) (tweezers are to be used for all handling of the collagen film).

2) Equilibrate the film in the controlled environment (22±2° C. and at 35±15% relative humidity) for at least 12 hours.
3) At least 5 minutes, but not more than 6 minutes after the last gush of the above acquisition test is absorbed, the cover plate and weights are removed, and the test sample (520) is carefully placed flat on a lab bench.
4) Four sheets of the precut and equilibrated collagen material (510) are weighed with at least one milligram accuracy, and then positioned centered onto the loading point of the article, and covered by Perspex plate (530) of 90 mm diameter, and about 20 mm thickness.
5) A weight (540) of 15 kg is carefully added (also centered).
6) After 30±2 seconds the weight and Perspex plate are carefully removed again, and the collagen films are reweighed.

The Post Acquisition Collagen Rewet Method value is the moisture pick up of the collagen film, expressed in mg.

It should be noted further, that this testing protocol can be adjusted easily according to specific product types, such as different diaper sizes, for use with other types of absorbent articles, such as adult incontinence devices, or catamenial devices. The type and amount of loading fluid, the amount and size of the absorbent material, or the applied pressure may also be varied to suit individual product needs. Such modifications will be obvious to one skilled in the art.

Teabag Centrifuge Capacity Test

While the Teabag Centrifuge Capacity Test (TCC test) has been developed specifically for superabsorbent materials, it can readily be applied to other absorbent materials.

The TCC test provides values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to ±0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately.

After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilized at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC =[(sample teabag weight after centrifuging), (blank teabag weight after centrifuging)−(dry absorbent material weight)] ÷(dry absorbent material weight)].

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 cm) the defines show how much averaging is taking place, naturally, the smaller the sample size, the less averaging will occur.

Lotion Transfer Measurement

Overview

This method uses a removable skin analog material that is placed on a wearer's skin for a controlled period of time. After the skin analog has been removed, it is extracted using an appropriate solvent and the amount of skin care composition deposited thereon is determined using known analytical methods. The method is described for use with lotioned infant diapers. One of skill in the art will recognize the appropriate changes for other skin care compositions, absorbent articles, or wearer types.

Subjects

Approximately equal numbers of male and female infants should be selected using the following inclusion and exclusion criteria. Sufficient infants should be selected to ensure that there are at least fifteen subjects per condition and transfer time who complete all aspects of the test.

Inclusion Criteria a. Healthy infant
b. Caregiver willing to not use lotions, creams, powders or other skin preparations in the diaper area for the duration of the test.
c. Infants who wear disposable diapers full time
d. Caregiver willing to give child bath the evening before the study and not again until after completion of the study
e. Caregiver will to have child refrain from swimming from the evening before the study until after completion of the study.
f. Preferably, infants who have infrequent bowel movements Exclusion Criteria a. The infant has been ill within the last four days
b. Diarrhea (soft stool) any time during the four days before the test
c. Medication which might increase frequency of bowel movements (e.g., oral antibiotics, anti fungal agents, corticosteroids)
d. Damaged skin in or around the test site (e.g., from sunburn, active dermal lesions, or the like)
e. Known allergies or irritation from adhesive or skin care ingredients Materials In Vivo Transfer Skin Analog: Dermatological Tape—TEGADERM Tape No. 1622W available from 3M Health Cares, St. Paul, Minn.

Sample Container Glass jar with closure available from VWR Scientific, West Chester, Pa. as catalog Number 15900-242

Tape Release Powder Baby powder (comprising only talc and fragrance) available from Johnson & Johnson, New Brunswick, N.J.

Surgical Gloves Available from Best Manufacturing Co., Menlo Ga., as product 6005PFM.

Extraction and Analysis

Extraction Solvent Dichloromethane, available from Sigma-Aldrich of St. Louis, Mo. as 27056-3

Steary alcohol Aldrich 25876-8

1-Hexadecanol Aldrich 25874-1

Dispensing Flask 10 ml

Gas Chromatograph Flame ionization Detector, Hewlett Packard Model 5890 is suitable.

Column Capillary column: Chrompack CP Sil-5 CB, 2 meters×0.25 mm id, 0.12 micron film thickness fused silica capillary (no substitutions)

Instrumental Data Must be able to reproducibly determine areas of peaks of System interest.

Method

In Vivo Transfer

A. Confirm from the subject's caregiver that the subject has been bathed within the last 24 hours and that no lotions, powders, etc. have been applied to the diapered region of the subject's skin since bathing.

B. Wearing the surgical gloves, place the subject on the table and remove his/her diaper.

C. Turn the subject on his/her stomach.

D. Remove the release liner from a TEGADERM tape and lightly brush J&J Baby Powder over the adhesive surface (Wear surgical gloves, or the like, during application to prevent contamination of the tape). Provide sufficient powder such that there is a light coat of powder over all of the tape except the edges. (This step is done to keep the tape from adhering too aggressively to the child's skin.).

E. FIGS. 3a and 3b illustrate placement location for the TEGADERM tape, shown in those figures as tape 700. Apply the tape 700 to the child's right buttock. The tape 700 is to be applied to the highest point on the child's buttock immediately adjacent to, but not in, the child's gluteal groove. A second tape 700 may be applied to measure transfer at two time increments or the effect of an additional diaper. If a second tape is used, apply the tape 700 on the left buttock using the procedure described above.

F. Change diapers according to the following protocol: 3 hour transfer time—1 diaper; 6 hour transfer time—2 diapers (change at 3 hours); 24 hour transfer times ad lib by caregiver. For 24 hour transfer times the following additional instructions are to be followed:

1. Use only water and a washcloth for cleaning the diapered area for the duration of the test. Do not use baby wipes. Avoid touching the area around the tapes with hands or any cleaning implement.

2. Do not use skin care products (lotions, ointments, creams, soap, etc.) for the duration of the test.

3. Do not bathe the subject for the duration of the test.

4. Use only the test diapers. Record the time of each diaper change.

5. Record the time of any bowel movement and clean the subject with water and a wash cloth.

G. Record the time each diaper was applied for all test diapers.

H. Recall the subject near the end of the predetermined transfer time.

I. Remove the test diaper. If the child has had a bowel movement, the study personnel should remove the tape 700 and discard it (the subject has then completed the test and data from that subject are not included in the analysis). If the subject has urinated, the tape 700 will be acceptable for analysis as described below.

J. Test facility personnel should wear surgical gloves and remove the tape 700 by grasping the edge of the tape 700 with tweezers and gently peeling the remaining portion of the tape 700 from the skin.

K. Place the used tape 700 in one of the glass jars and close the lid. Make sure the jar is properly labeled for subsequent sample identification.

L. At the completion of the test collect all of the samples in the jars for analysis as described below.

Extraction and Analysis

This method is designed for use with the preferred skin care composition, the skin care composition of Example 3. One of ordinary skill in the art will recognize what adaptations may be necessary to extract and analyze the level of other skin care compositions. In principle: 1) one of the major ingredients of the composition is extracted from the skin analog using an appropriate solvent; 2) gas chromatographic or other appropriate quantitative analytical techniques are then used to determine the level of the major ingredient in the extract; 3) amount of skin care composition is calculated per unit area based on amount of major ingredient in extract and the area of the tape.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract skin care composition from the tapes. When not being used, this container should be kept tightly capped to prevent evaporation of solvent.

Calibration Standard

Prepare a calibration standard of known concentration by accurately weighing (±0.1 mg) 10±1 mg of the stearyl alcohol into a 100 ml volumetric flask. Record the weight of stearyl alcohol used. Add the internal standard/extraction solvent to the flask and mix to dissolve. Fill to volume and mix well. When not being used, this container should be kept tightly capped to prevent evaporation of solvent. This solution will be used to determine the relative response of the stearyl alcohol to the hexadecanol internal standard for calibration of the instrument.

Preparation and Calibration of the Gas Chromatograph

All equipment should be installed, operated and maintained according to manufacturer's recommendations.

Install the column and check all the gas flows with the column oven at 100° C. and the injection port and detector at operating temperatures. The GC will be operated under the following conditions:

Carrier Gas: Hydrogen (Helium may be used); flow rate 1.5 ml/min

Injection Port: 325° C.; Split vent flow 30 ml/min; Septum purge 2 ml/min; straight through liner with glass wool plug; Merlin microseal.

Injection volume: 2 $\mu$l split

FID Detector: 350° C.; set gas flows according to manufacturer suggestions. Typical gas flows are 400 ml/minute for air, 30 ml/minute for hydrogen and 30 ml/minute for the auxiliary (make up) gas.

Column Oven: 100° C. ramped at 15° C./minute to 325° C.; hold for 10 minutes

Insure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram. If extraneous peaks are present or baseline is not suitable, trouble shoot and correct problem(s).

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure

1) Remove the lid from the sample jar and add 10 ml of the extraction solvent/internal standard solution using the dispensing flask. Replace the cap and swirl the contents to insure that the tape 700 is not adhering to the sides of the jar and is totally submersed in solvent. Repeat for all samples.

2) Allow the samples to sit 16 hours (typically done overnight).

3) Swirl the contents of the jar to mix. Using a transfer pipette, transfer an aliquot of the sample extract to a properly labeled autosampler vial. Cap the vial. Replace jar lid and retain until analyses are complete. Repeat for all samples.

4) Place the vials in the autosampler in random order and start the analyses using the GC conditions described above. The first vial should be a dichloromethane blank. Several "check" standards should be placed (about every 20th sample) through out the run to verify correct operation.

5) At the completion of the run, check each chromatogram to insure proper analysis. If a problem is suspected, trouble shoot and correct. Reanalyze samples as needed.

Calculations

The total micrograms of stearyl alcohol in each sample extract is calculated based on the relative response of the stearyl alcohol peak to that of the 1-hexadecanol internal standard. The ratio of the peak areas is multiplied by the relative response factor (determined at time of instrument calibration) and the micrograms of internal standard in the extract to yield the total $\mu$g of stearyl alcohol in a sample.

Instrument Calibration

Determine the instrumental relative response factor for the stearyl alcohol and the internal standard based on the areas of the stearyl alcohol and 1-hexadecanol peaks in the calibration standard chromatogram.

$$\text{Response factor } (R_f) = \frac{Area_{inst}}{weight_{inst}} \times \frac{weight_{sa}}{Area_{sa}} \times 10$$

where $Area_{inst}$ GC peak area for the internal standard in the calibration standard $Area_{sa}$ GC peak area for the stearyl alcohol in the calibration standard $weight_{inst}$ actual micrograms of the internal standard used to prepare internal standard/extraction solvent $weight_{sa}$ micrograms of the stearyl alcohol used to prepare the calibration standard Test Sample Calculations Calculate the total micrograms of stearyl alcohol in each test sample using the peak areas from the test sample chromatogram in the following equation:

$$\text{Total } \mu g \text{ SA} = \frac{Area_{sa}}{Area_{inst}} \times R_f \times \frac{weight_{inst}}{100}$$

where $Area_{inst}$ GC peak area for the internal standard in the test sample $Area_{sa}$ GC peak area for the stearyl alcohol in the test sample $weight_{inst}$ actual micrograms of the internal standard used to prepare internal standard/extraction solvent Report amount of skin care composition transferred in mg/cm² where:

$$\text{Composition Transferred} = \frac{0.1 \times \mu g \text{ of stearyl alcohol}}{(\% \text{ stearyl alcohol in composition}) \times (\text{tape area})}$$

For the method described above the concentration of stearyl alcohol in the composition is 41% and the tape patch measures 4.4 centimeters×4.4 centimeters.

Therefore

Composition Transferred=(0.001×$\mu$g of stearyl alcohol)/(0.41×4.4 cm×4.4 cm)

0.000126×$\mu$g of stearyl alcohol (mg/cm²)

Skin Hydration Measurement Test

Overview

This method is suitable for technical investigation of the effect of diaper products on skin hydration. The test measures hydration of adult skin that has been occluded using a diaper product for a controlled amount of time as an in vivo model of similar effects on infant skin. The test is based on methodology that is broadly used by the art to measure skin hydration. Adult subjects are used rather than infants because: 1) adult subjects can be instructed and 2) adult subjects are better able to control their movement during the test with a resulting reduction in test variability.

This test is a randomized, paired comparison test where each subject serves as her own internal control. Eighteen (18) qualified female subjects per test condition receive an application of a test diaper product to each volar forearm for two hours. For evaluation of the effect of a topsheet, prior to diaper product application, one arm may receive an application of a test lotion at a predetermined level. The diaper product will then be loaded three times during the two hour period, followed by a 20-minute measurement period. Such testing should be conducted at a qualified clinical research organization (CRO) and should comply with good clinical practices (GCPs).

Method

General Discussion

Subjects will enter and remain for the duration of the test in an environmentally controlled room with a temperature of 20–25° C. and a relative humidity (% RH) of 40%±5%. Records of temperature and humidity are maintained at the research site.

Figure 4A:
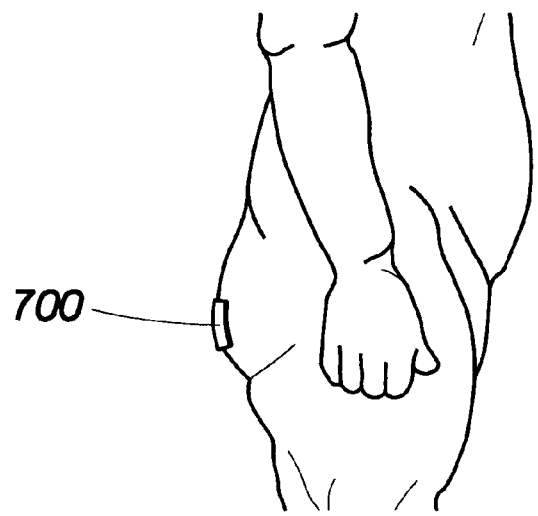
FIG. 4A is a side view showing placement of the skin analog used in the lotion transfer test.
Figure 4B:
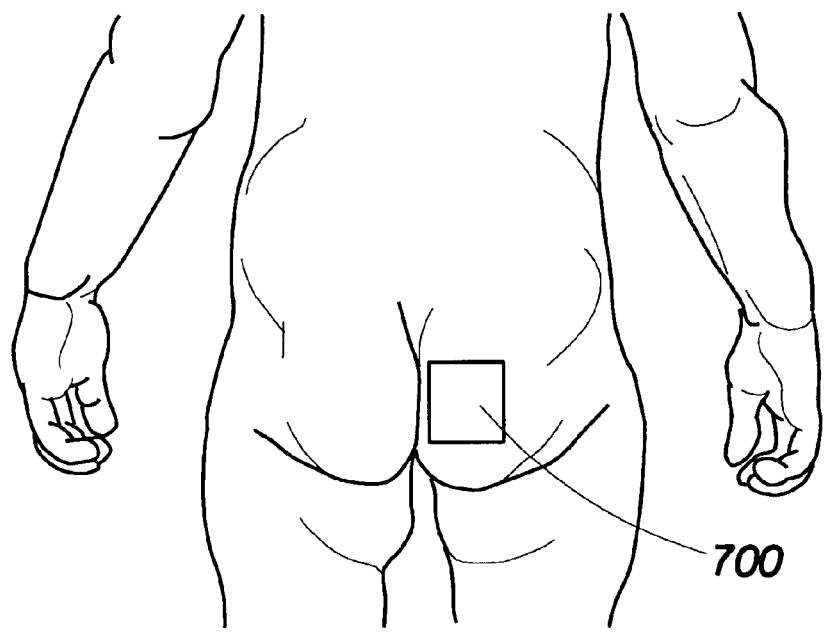
FIG. 4B is a plan view showing placement of the skin analog used in the lotion transfer test.

Depending on the test products being considered, female subjects who qualify to receive the test materials may receive an application of a diaper product on one volar forearm, on both volar forearms, lotion to one volar forearm 600 and a diaper product to both volar forearms, or other combination as may be required for comparison of skin hydration. When lotion is used, it is pre-measured and applied by a technician to the center of the test area 610 which is located about halfway between a subject's wrist and elbow 620 as shown in FIG. 4 and spread using a circular motion until the entire area 620 is covered. Each diaper is loaded with approximately 70 mls of a sterile saline solution on initial application and again at 40 80-minute intervals during a 120-minute application period. Diapers are worn for the entire two hour period. Water evaporation rates are measured at several time points before and after diaper treatment on each volar forearm. Water evaporation rates (TEWL) are measured using a ServoMed Evaporimeter.

All equipment should be calibrated prior to starting the test. Between readings, allow the ServoMed Evaporimeters to calibrate on their own. Pumps should be calibrated following each subject to be sure they are delivering the required 70 ml. The warm bath should be turned on and filled with the sterile saline solution at least 30 minutes prior to the first loading each day so the temperature can be brought up to the required setting (37±0.2 degrees Celsius). In addition, the saline should be changed daily.

Pre-Wrap Procedures

Figure 5:
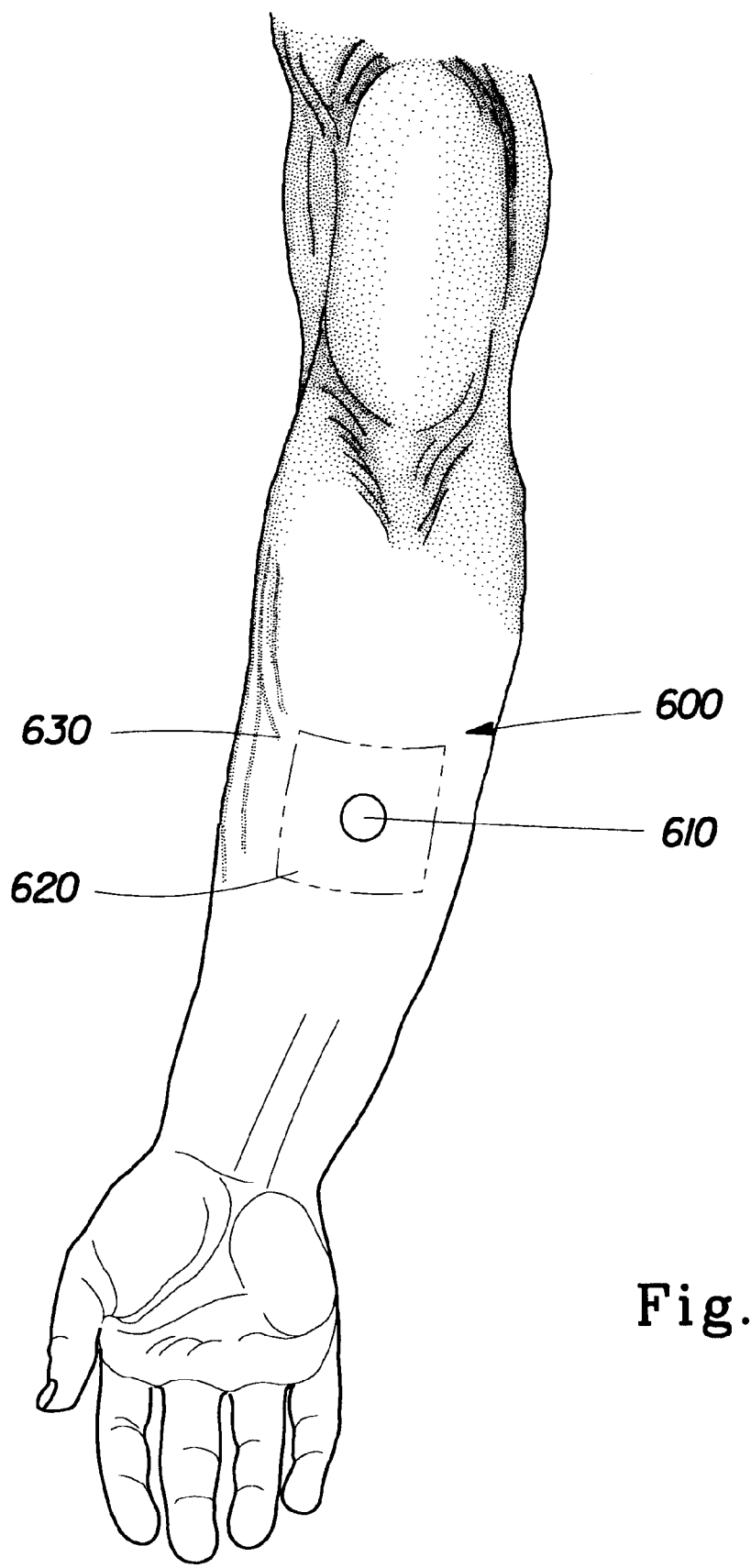
FIG. 5 is a schematic drawing showing the positions of sample sites for the Skin Hydration Measurement Test described in the TEST METHODS section.

Each volar forearm will serve as a test area. The forearm should be marked using a template indelible markers prior to application of the test article (FIG. 5). The area to be marked should be 2 inches×2 inches (5 centimeters×5 centimeters). A 0.5 inch (1.25 centimeter) circle should be marked in the center of this area. The template for marking measurement area is centered on the forearm by using the midpoint 630 between the elbow and wrist as the midpoint of the marking template.

Each subject will have a 30-minute equilibration period in the temperature/humidity controlled room prior to being treated. At the end of the equilibration period, baseline TEWL measurements are obtained from each subject by placing the evaporimeter probe within the marked circle on each arm prior to application of the test material(s). The evaporimeter probe is left on the skin for 60 seconds with data being collected after the first 20 seconds. See FIG. 5.

Lotion

When lotions are one of the test conditions, one test area is coated with a pre-weighed amount of lotion product, prior to application of the diaper product to the volar forearms. Lotion is weighed out using a four place scientific balance. The amount of lotion as weighed should yield the desired dose level (mg/in$^2$ or mg/cm$^2$) when applied to the entire test area 620. Lotion is weighed separately for each subject and the actual weight recorded on the data collection form.

Lotion is applied by a technician at the center 610 of the pre-marked template and applied in a circular motion until the entire square test area 620 is evenly coated. Gloves (latex or vinyl type) should be used for applying lotion to avoid contamination of the lotion product. Post-lotion baseline measurements are taken 5 minutes±30 seconds following lotion application (immediately prior to application of the diaper product) by placing the evaporimeter probe within the marked circle. The evaporimeter probe is left on the skin for 60 seconds with data being collected after the first 20 seconds. The "post-lotioned" baseline measurement is done approximately five minutes after the initial baseline measurement on the non-lotioned arm to maintain consistency in timing for both arms.

Arm Wrap Procedures

This procedure involves application of diaper product to each test area.

Weigh each diaper before wrapping and loading. Diapers have been pre-marked inside and outside with 2 inch by 2 inch (6 cm by 6 cm) squares. These will correspond to the loading area and are wrapped directly over a similar mark on the forearm. Place the end of the dispensing tube on the mid-forearm (approx. center of the premarked area) Then, place the armband on the subject with the target loading zone, marked on the outer side of the diaper, directly over the end of the dispensing tube. NOTE: Both arms are wrapped with diapers (one diaper per arm), one at a time, always starting with the left arm. The diapers are wrapped with consistent pressure for each panelist. Products codes are randomized for each panelist. The eye of the dispensing tube should be facing the diaper. Hold armband in place by fastening the tapes on the diaper to the diaper, then securing with additional adhesive tape as necessary. The end of the diapers are folded so they do not overlap the loading and measurement areas.

Diaper application is staggered over time to insure that removal times are sufficiently separated from each other to allow timely execution of all subsequent evaluations. Time zero for arm band application is defined as the moment when taping of the arm band to the skin is complete.

Loading Procedures

The diaper is loaded with approximately 70 mls of a sterile saline (0.9% sodium chloride) solution three times during the course of a 2 hour period (120 minutes). The saline is kept in a warm water bath to ensure it is warmed to body temperature (37±0.2 degrees C.). The test articles are loaded using a Masterflex pump set to deliver 10 ml solution per second. Each pump is fitted with plastic tubing with a dispensing nozzle to direct the saline into the test article attached. Loading is done immediately after application of the test article, at 40 minutes and again at 80 minutes. During loading, the loading area should be turned so the volar part of the forearm is facing the floor. The nozzle is inserted and positioned directly between the skin and the diaper in the demarcated areas. The nozzle is oriented so the stream delivers the solution into the diaper surface. The nozzle is removed and reinserted for the next loading. At the end of the 2-hour period the diapers are removed and TEWL measurements made at the designated site within the test area 620.

TEWL Procedures

Immediately following diaper removal, place the probe of the Servo Med Evaporimeter (See Observations and Measurements section below) on the subject's forearm at the same sites where the baseline readings were taken and begin data collection. The evaporimeter probe is left on the skin for 60 seconds with data being collected after the first 20 seconds. Measurements are taken at 0, 5, 10, 15, and 20 minutes following armband removal.

Data Analysis

TEWL values collected serially over time can be analyzed by evaluating the total area defined by the TEWL decay curve (AUC). This calculation is based on the assumption that TEWL values will eventually decay to a baseline level (as estimated by the post-lotion baseline reading) approximately following an exponential decay curve:

$$f(t) = c \times e^{dt}$$

where: c represents the initial height of the curve at time 0 and d represents the rate of decay. The total area (AUC) between the x axis and such a curve (extrapolated to infinity)

is an approximation of the total hydration. These factors and the corresponding AUC can be determined for each treatment site and subject as follows:

1) Subtract the baseline value from each of the TEWL measurements taken at 0, 5, 10, 15, and 20 minutes. If any TEWL value is smaller than its corresponding baseline value, then use a modified baseline value calculated as 0.99 multiplied times the smallest of the 0, 5, 10, 15, and 20 minute TEWL values.

2) Calculate the natural log for each difference.

3) Fit a regression line utilizing known mathematical techniques, such as least squares, using each time point as an x value and the log transformed difference in TEWL value at this time point as a y value.

4) Calculate AUC in $g/m^2$ as:

$$AUC = -60 \times (e^a)/b$$

where a is the intercept and b the slope determined by step 3.

5) Calculate the difference in AUC between the test treatment site and the control treatment site.

The test minus control site AUC differences may be analyzed using a paired t-test or, if the AUC differences do not appear to be normally distributed, a nonparametric test (e.g., Wilcoxon's Signed Rank Test) may be used.

To evaluate the immediate effect of a treatment on skin surface moisture, $t_0$ TEWL values (where $t_0$ is the TEWL measurement made immediately after removing the diaper) corrected for baseline (i.e., $t_0$—post-lotion baseline) also may be compared between treatments by paired t-test.

An alternate means to compare treatment differences on skin hydration is Normalized Integrated Vapor Flux which shows the relative hydration of test and control conditions. Normalized Integrated Vapor Flux may be calculated as follows:

1) Determine an AUC value for each test condition (forearm) and each control condition (opposed forearm) and determine the average AUC for the test ($AUC_{test}$) and control ($AUC_{ctl}$) conditions.

2) Calculate the Normalized Integrated Vapor Flux as:

$$(AUC_{test})/(AUC_{ctl}) \times 100$$

Test Population

Eighteen (18) healthy adult female subjects per test condition are used. During testing, a subject's hand and arm movement is limited to low or no movement activities such as reading. Activities such as writing and knitting will not be permitted.

Inclusion Criteria a. Healthy adult female ages 18 to 55.
b. Subjects should wear short sleeves or sleeveless clothing.
c. Subjects are willing to rest in the Evaporimeter measurement room for approx. 30 minutes before the baseline measurements are taken and for the required testing period.
d. Subject agrees to refrain from using body washes or soaps which contain moisturizers beginning the evening prior to the test.
e. Subject agrees to refrain from using lotions, creams or skin moisturizers beginning the evening prior to the test.

Exclusion Criteria a. History of atopy or other chronic dermatological conditions.
b. Damaged skin in or around the test site, including sunburn, active dermal lesions or scars.
c. Smoking within two hours of the baseline TEWL readings and/or before the last evaporimeter measurement is finished.
d. Bathing, washing or swimming within two hours of the baseline TEWL reading and/or during the test period before the last evaporimeter measurement is finished.
e. Caffeine within two hours of the baseline TEWL reading and/or during the test period before the last evaporimeter measurement is finished.
f. Perfume or cream/lotion applied on either forearm during the test period and/or before the last evaporimeter measurement is finished.
g. Medication which might influence the skin condition, e.g. corticosteroids taken orally or topically applied on the measurement site.
h. Physical work after diaper armband application which might cause sweating. Subjects will remain at the test center under the direct supervision of the test staff throughout the test. Subjects are confined to a chair in order to keep movement and exertion to a minimum.

Test Materials

Specific test materials are defined by the experimental conditions.

Observations and/or Measurements

Trans Epidermal Water Loss (TEWL)

The primary measurement method is TEWL measurement using the ServoMed Evaporimeter (suitable apparatus is available from Servomed AB, Stockholm, Sweden as Model EP1). The apparatus should be calibrated and operated according to the manufacturer's instructions. Measurements are taken at baseline (prior to armband application), 5 minutes after lotion application (for tests where a lotion is one of the conditions), 0 minutes after armband removal, and then again at 5, 10, 15 and 20 minutes after armband removal. These measurements are taken for 60 seconds with data being collected after the first 20 seconds. The remaining 40 seconds of data are averaged by the evaporimeter software to give a mean TEWL value ($gm/m^2/hr$). If data are manually collected, an average of the 40, 50 and 60 second readings should be used.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for absorption of bodily fluids deposited by a wearer, said absorbent article comprising:

a. a body contacting surface having a skin care composition that is transferred from said body contacting surface to said wearer's skin by contact, normal wearer motion and/or body heat at a level effective in providing a skin condition benefit to said wearer's skin;

b. a liquid impermeable backsheet, wherein said backsheet comprises a first zone having a mass vapor transmission rate value of at least about 1300 $g/m^2/24$ hr; and c. an absorbent core positioned between said body contacting surface and said backsheet, wherein said absorbent core has a post acquisition collagen rewet value and the ratio of said post acquisition collagen rewet value to said mass vapor transmission rate value is less than about 0.05 mg/(g/m$^2$/24 hr).

2. An absorbent article according to claim 1 wherein said backsheet comprises two or more zones, and at least one of the remaining zones has a mass vapor transmission rate value greater than said mass vapor transmission rate value in said first zone.

3. An absorbent article according to claim 1 wherein said body contacting surface comprises a topsheet.

4. An absorbent article according to claim 1 wherein said body contacting surface comprises an elastic leg cuff.

5. An absorbent article according to claim 1 wherein said body contacting surface comprises an elastic waist feature.

6. An absorbent article according to claim 1 wherein at least about 0.07 mg/cm$^2$ of said skin care composition is transferred from said body contacting surface to said wearer's skin by normal wearer motion and/or body heat.

7. An absorbent article according to claim 1 wherein said absorbent article has a normalized integrated vapor flux and said skin care composition provides a reduction in said normalized integrated vapor flux of at least about 5 percent.

8. An absorbent article according to claim 7 wherein said skin care composition provides a reduction in said normalized integrated vapor flux of at least about 27 percent.

9. An absorbent article according to claim 1 wherein said absorbent core has a post acquisition collagen rewet value and said skin care composition causes said post acquisition collagen rewet value of said absorbent core to be reduced by at least about 35 mg.

10. An absorbent article according to claim 1 wherein said ratio is less than about 0.04 mg/(g/m$^2$/24 hr).

11. An absorbent article according to claim 1 wherein said ratio is less than about 0.03 mg/(g/m$^2$/24 hr).

12. An absorbent article according to claim 1 wherein said ratio is less than about 0.019 mg/(g/m$^2$/24 hr).

13. An absorbent article according to claim 1 wherein said body contacting surface comprises a side panel.

14. An absorbent article for absorption of bodily fluids deposited by a wearer, said absorbent article comprising:
   a. a liquid permeable topsheet having a lotion disposed on a body contacting surface thereof, wherein said lotion is transferred from said body contacting surface to said wearer's skin by contact, normal wearer motion and/or body heat at a level for reducing skin overhydration;
   b. a liquid impermeable backsheet, wherein said backsheet comprises a first zone having a mass vapor transmission rate value of at least about 1300 g/m$^2$/24 hr; and
   c. an absorbent core positioned between said body contacting surface and said backsheet; wherein said absorbent core has a post acquisition collagen rewet value and ratio of said post acquisition collagen rewet value to said mass vapor transmission rate value is less than about 0.05 mg/(g/m$^2$/24 hr).

15. An absorbent article according to claim 14 wherein at least about 0.07 mg/cm$^2$ of said lotion is transferred from said body contacting surface to said wearer's skin by normal wearer motion and/or body heat.

16. An absorbent article according to claim 14 wherein said lotion has a zero shear viscosity between about $1.0 \times 10^6$ centipoise and about $1.0 \times 10^8$ centipoise.

17. An absorbent article according to claim 14 wherein said absorbent article has a normalized integrated vapor flux and said skin care composition provides a reduction in said normalized integrated vapor flux of at least about 5 percent.

18. An absorbent article according to claim 14 wherein said absorbent core has a post acquisition collagen rewet value and said lotion causes said post acquisition collagen rewet value of said absorbent core to be reduced by at least about 35 mg.

19. An absorbent article according to claim 14 wherein said ratio is less than about 0.019 mg/(g/m$^2$/24 hr).

* * * * *

UNITED STATES PATENT AND TRADEMARK OFFICE
CERTIFICATE OF CORRECTION

PATENT NO. : 6,107,537
DATED : August 22, 2000
INVENTOR(S) : Elder et al.

Page 1 of 4

It is certified that error appears in the above-identified patent and that said Letters Patent is hereby corrected as shown below:

Column 1,
Line 23, please delete "wearers" and insert therefor -- wearer's --.
Line 50, after "rash" and before "[a]n, insert therefor -- as --.
Line 51, after perineum, insert therefor -- , -- (a comma).

Column 4,
Line 10, please delete "glm$^2$ and insert therefor -- g/m$^2$ --.
Line 23, please delete "acquisition" and insert therefor -- Acquisition --.
Line 50, "please delete "composed" and insert therefor -- composted --.

Column 7,
Lines 56-57, please delete "hydro-philicing" and insert therefor -- hydrophilizing --.

Column 9,
Line 24, please delete "hydrocoloids" and insert therefor -- hydrocolloids" --.

Column 11,
Line 45, after the second occurrence of "about", please delete "," (the comma).
Lines 58-59, please delete "g 24 h/m$^2$" and insert therefor --g/24/ h/m$^2$ --.

Column 12,
Line 7, please delete "there" and insert therefor -- the --.
Line 11, after "also" and before "least", insert therefor -- at --.
Line 17, please delete "EXXARE" and insert therefor -- EXXAIRE --.
Line 23, please delete "polymerize." and insert therefor -- polymeric --.
Line 29, after "in" and before "directions", insert therefor -- CD --.

Column 14,
Line 14, please delete "skilled" and insert therefor -- skill --.
Line 28, please delete "30" and insert therefor -- as --.
Line 30, please delete "hydroformer" and insert therefor -- hydroformed --.
Line 33, please delete "comprise" and insert therefor -- comprised --.

Column 15,
Line 30, after "nonocclusive" and before "function", please delete "," (the comma).
Line 34, after "indirectly" and before "skin", insert "," (a comma).
Line 39, please delete "referral" and insert therefor -- refers --.
Line 54, after "composition" and before "dictate" insert therefor -- will --.

UNITED STATES PATENT AND TRADEMARK OFFICE
CERTIFICATE OF CORRECTION

PATENT NO. : 6,107,537
DATED : August 22, 2000
INVENTOR(S) : Elder et al.

It is certified that error appears in the above-identified patent and that said Letters Patent is hereby corrected as shown below:

Column 17,
Line 12, please delete "Vaselinerdrzl" and insert therefor -- Vaseline --.
Line 15, "please delete "UrltrJiL" and insert therefor -- Ultra --.

Column 18,
Line 30, please delete "title" and insert therefor -- the --.
Line 34, please delete "fume" and insert -- fumed --.
Lines 41-42, please delete "wear-ers" and insert therefor -- wearer's --.
Line 49, after "using" and before "a", please delete "," (the comma).
Line 51, please delete "Merlrose" and insert therefor -- Melrose --.

Column 19,
Line 9, after "thereof" please delete "," and insert therefor --; -- (a semi-colon).
Line 10, after the first occurrence of "thereof", please delete "," and insert therefor -- ; -- (a semi-colon).
Line 13, after "thereof" please delete "," and insert therefor -- ; -- (a semi-colon).

Column 20,
Line 16, after "alkaryl" and before "arakyl", insert therefor -- , -- (a comma).
Line 23, please delete "silanes" and insert therefor -- silaceous --.

Column 21,
Line 51, please delete "processing converting" and insert therefor -- processing/converting --.
Line 59, please delete "solublized" and insert therefor -- solubilized --.

Column 22,
Line 58, after "thereof" please delete "," and insert therefor -- ; -- (a semi-colon).

Column 23,
Line 13, after "acid" and before "sorbitan", please delete "," (the comma).
Line 49, delete "allyl" and insert therefor -- alkyl --.
Line 64, delete "dextrosie" and insert therefor -- dextrose --.

Column 24,
Line 3, after [(CHOH) $_{n-1}$, delete the "[" (left bracket) and insert therefor -- ]—(right bracket).
Line 5, after "is" insert therefor -- H --, and delete "for."
Line 10, after "N-2-hydroxypropyl" insert therefor -- . -- (a period).
Line 11, delete "oleamidie" and insert therefor -- oleamides --.
Line 15, "1-deoxyrmaltotriotityl" and insert therefor -- 1-deoxymaltotriotityl --.

UNITED STATES PATENT AND TRADEMARK OFFICE
CERTIFICATE OF CORRECTION

PATENT NO. : 6,107,537
DATED : August 22, 2000
INVENTOR(S) : Elder et al.

It is certified that error appears in the above-identified patent and that said Letters Patent is hereby corrected as shown below:

Column 25,
Line 4, delete "inrumobriliing" and insert therefor -- immobilizing --.
Line 27, after "than" delete "a".
Line 34, after "HLB" delete ":" (the colon).
Line 40, delete "Sirmnilarly" and insert therefor -- Similarly --.
Line 67, after 30, delete the left quotation mark (").

Column 26,
Line 18, delete "allyl" and insert therefor -- alkyl --.
Line 45, after "also" delete "," (the comma).
Line 48, after "mixtures" delete "thereorf" and insert therefor -- thereof, --.

Column 29,
Line 46, delete "regards" and insert therefor -- regard --.
Line 47, delete "articles's" and insert therefor -- article's --.

Column 30,
Line 48, delete "appropgriate" and insert therefor -- appropriate --.

Column 31,
Line 9, after "as" delete "," (the comma).
Line 11, delete "there" and insert therefor -- the --.

Column 33,
Line 18, delete "have" and insert therefor -- are --.
Line 22, after "MVTR" delete "." (the period).

Column 35,
Line 17, delete "Varn" and insert therefor -- Van --.
Line 29, before "reference" insert therefor -- by --.

Column 36,
Line 1, delete "cell", and after "stiffened" insert therefor -- cellulose layer 28b. Specifically, a high- --.
Line 5, delete "arwrvdth" and insert therefor -- a width --.
Line 14, after "SXM" please insert "," (a comma).

UNITED STATES PATENT AND TRADEMARK OFFICE
CERTIFICATE OF CORRECTION

PATENT NO. : 6,107,537
DATED : August 22, 2000
INVENTOR(S) : Elder et al.

It is certified that error appears in the above-identified patent and that said Letters Patent is hereby corrected as shown below:

Column 39,
Line 21, after the first occurrence of "the", delete ")" (right parenthesis), and after "test", delete ":" (the colon).
Line 62, delete "up" and insert therefor -- "cup" --.

Column 40,
Line 13, delete "Chermical" and insert therefor -- Chemical --.
Line 37, delete "g24 h/mrz" and insert therefor -- $g/24h/m^2$ --.
Line 42, delete the first occurrence of "that" and insert therefor -- the --.

Column 42,
Line 6, delete "bout" and insert therefor -- about --.
Line 8, after "gush" delete "," (the comma).

Column 46,
Line 49, before "hexadecanol" insert therefor -- 1- -- (number 1 and a dash).

Column 49,
Line 11, after "40" insert therefor -- -and -- (a dash and the word "and").

Column 51,
Line 24, after "t-test" insert therefor -- , -- (a comma).

Signed and Sealed this

Eleventh Day of December, 2001

Attest:

*Nicholas P. Godici*

NICHOLAS P. GODICI
*Attesting Officer*  *Acting Director of the United States Patent and Trademark Office*